United States Patent
Vargheese et al.

(10) Patent No.: US 10,558,784 B2
(45) Date of Patent: Feb. 11, 2020

(54) TIME AND MOTION DATA FUSION FOR DETERMINING AND REMEDYING ISSUES BASED ON PHYSICAL PRESENCE

(71) Applicant: Cisco Technology, Inc., San Jose, CA (US)

(72) Inventors: Rajesh Vargheese, Austin, TX (US); Carlos M. Pignataro, Raleigh, NC (US); James D. Stanley, III, Austin, TX (US); Prashant R. Prabhudesai, Allen, TX (US); Matthew R. Engle, Plano, TX (US); Gonzalo A. Salgueiro, Raleigh, NC (US)

(73) Assignee: Cisco Technology, Inc., San Jose, CA (US)

( * ) Notice: Subject to any disclaimer, the term of this patent is extended or adjusted under 35 U.S.C. 154(b) by 964 days.

(21) Appl. No.: 14/845,771

(22) Filed: Sep. 4, 2015

(65) Prior Publication Data
US 2017/0068793 A1    Mar. 9, 2017

(51) Int. Cl.
*G06F 19/00* (2018.01)
*G16H 10/60* (2018.01)

(52) U.S. Cl.
CPC ........ *G06F 19/3418* (2013.01); *G06F 19/328* (2013.01); *G16H 10/60* (2018.01)

(58) Field of Classification Search
CPC ..... H04W 64/00; H04W 4/02; H04W 64/003; G16H 50/20; G06F 15/16; G06Q 10/1093
USPC ....................... 705/2–4; 455/456.1
See application file for complete search history.

(56) References Cited

U.S. PATENT DOCUMENTS

| | | | |
|---|---|---|---|
| 5,959,662 A | 9/1999 | Shaffer et al. | |
| 8,754,925 B2 | 6/2014 | Ng et al. | |
| 8,908,903 B2 | 12/2014 | Deng et al. | |
| 2002/0052760 A1* | 5/2002 | Munoz | G06F 19/3418 705/2 |
| 2007/0174088 A1 | 7/2007 | Koo et al. | |
| 2008/0181140 A1* | 7/2008 | Bangor | H04L 12/1818 370/261 |
| 2009/0109033 A1* | 4/2009 | Salvat | G01S 5/0027 340/572.1 |
| 2009/0193267 A1 | 7/2009 | Chung | |

(Continued)

FOREIGN PATENT DOCUMENTS

WO    WO-2008084304 A1 *    7/2008    ......... H04L 12/1822

OTHER PUBLICATIONS

Sauter, Martin, "From GSM to LTE: An Introduction to Mobile Networks and Mobile Broadband," p. 160 (Year: 2011).*

(Continued)

*Primary Examiner* — John P Go
(74) *Attorney, Agent, or Firm* — Edell, Shapiro & Finnan, LLC

(57) ABSTRACT

A plurality of time and motion data sets are correlated at a network connected device. The time and motion data sets track an item of interest, and at least one of the time and motion data sets comprises energy consumption data or wireless local area network location data. Physical presence for the item of interest is determined based upon the correlating of the multiple time and motion data sets. Based upon the physical presence of the item of interest, an unacceptable condition for the item of interest may be determined. The unacceptable condition for the item of interest is remedied.

20 Claims, 15 Drawing Sheets

(56) References Cited

U.S. PATENT DOCUMENTS

| | | | | | |
|---|---|---|---|---|---|
| 2009/0259492 | A1* | 10/2009 | Cossman | .............. | G06F 19/328 705/3 |
| 2010/0031334 | A1* | 2/2010 | Shaikh | ................... | G06F 21/35 726/7 |
| 2010/0135178 | A1* | 6/2010 | Aggarwal | ............. | G01S 5/0205 370/252 |
| 2011/0090081 | A1* | 4/2011 | Khorashadi | ........... | G01S 5/0252 340/539.13 |
| 2012/0042366 | A1* | 2/2012 | Jin | ........................ | G06Q 50/24 726/7 |
| 2012/0303386 | A1 | 11/2012 | Zavaleta et al. | | |
| 2013/0332197 | A1* | 12/2013 | Hinkel | ................... | G06Q 50/24 705/3 |
| 2014/0064471 | A1* | 3/2014 | Krishnan | .............. | H04M 3/567 379/202.01 |
| 2014/0241515 | A1* | 8/2014 | Oswal | ..................... | H04M 3/56 379/93.01 |
| 2014/0280955 | A1* | 9/2014 | Stuntebeck | ........... | H04L 63/107 709/226 |
| 2015/0103136 | A1* | 4/2015 | Anderson | ............... | H04L 12/18 348/14.09 |
| 2015/0365403 | A1* | 12/2015 | Counterman | ....... | H04L 63/0876 726/9 |
| 2015/0379441 | A1* | 12/2015 | Syed | .................. | G06Q 10/0631 705/2 |

OTHER PUBLICATIONS

Sauter, Martin, "From GSM to LTE: An Introduction to Mobile Networks and Mobile Broadband," 2011 (Year: 2011).*

Yoshimi, Billibon "A Multimodal Speaker Detection and Tracking System for Teleconferencing," Multimedia '02, Dec. 1-6, 2002 (Year: 2002).*

\* cited by examiner

TIME AND MOTION DATA FUSION FOR DETERMINING AND REMEDYING ISSUES BASED ON PHYSICAL PRESENCE

TECHNICAL FIELD

The present disclosure relates to the acquisition and processing of multiple time and motion data sets.

BACKGROUND

Time and motion analytics are the evaluation of work systems involving the movement of people, data, and equipment over time. Time and motion use cases were originally performed by filming and analyzing, for example, the motion of bricklaying and the work habits of clerical employees. As technology has progressed, the sophistication and complexity of these studies have expanded into numerous industries.

Time and motion analyses can be used to create powerful data sets that provide a deeper and more complete understanding of movement and work systems. Yet, when these data sets are created, they are normally created for narrowly focused use cases.

DESCRIPTION OF EXAMPLE EMBODIMENTS

Overview

A plurality of time and motion data sets are correlated at a network connected device. The time and motion data sets track an item of interest, and at least one of the time and motion data sets comprises energy consumption data or wireless local area network location (e.g., Wi-Fi®) data. Physical presence for the item of interest is determined based upon the correlating of the multiple time and motion data sets. Based upon the physical presence of the item of interest, an unacceptable condition for the item of interest may be determined. The unacceptable condition for the item of interest is remedied.

Example Embodiments

Figure 1:
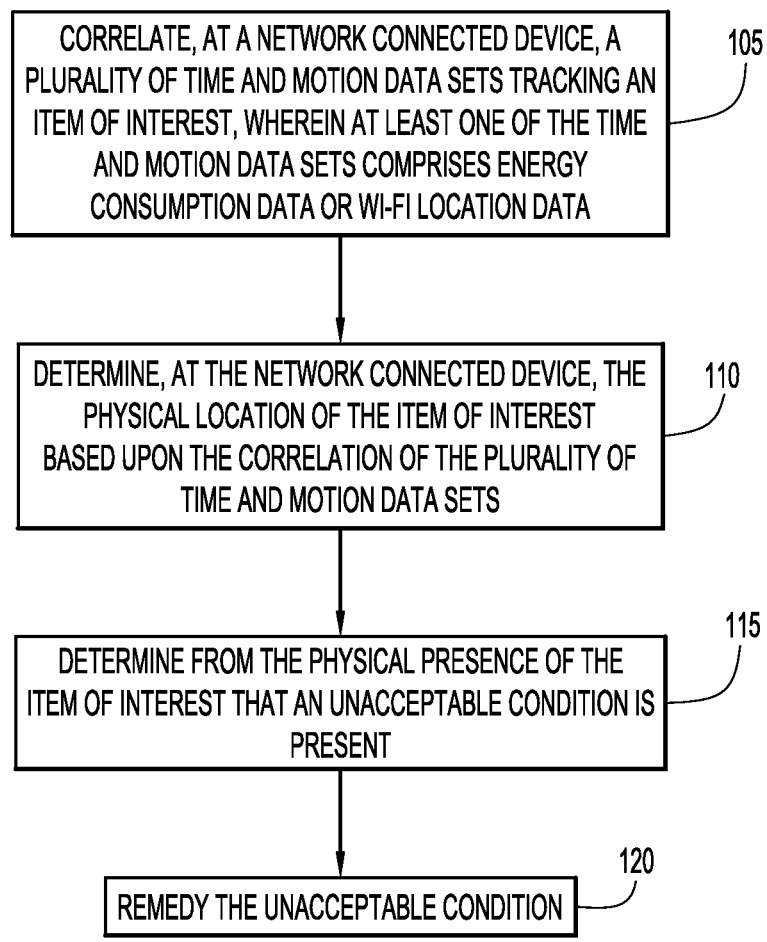
FIG. 1 is a block diagram illustrating a process for using time and motion data sets to determine and remedy issues based on physical presence, according to an example embodiment.

With reference now made to FIG. 1, depicted therein is a flowchart illustrating a process for remedying unacceptable conditions for items of interest using multiple time and motion data sets that may be used to determine physical presence. The process of flowchart 100 begins in operation 105 where a plurality of time and motion data sets are correlated at a network connected device. The time and motion data sets track an item of interest, and at least one of the time and motion data sets comprises energy consumption data or Wi-Fi location data. In operation 110, physical presence for the item of interest is determined based upon the correlating of the multiple time and motion data sets. In operation 115, based upon the physical presence of the item of interest, an unacceptable condition for the item of interest may be determined. Finally, in operation 120, the unacceptable condition for the item of interest is remedied.

Figure 2:
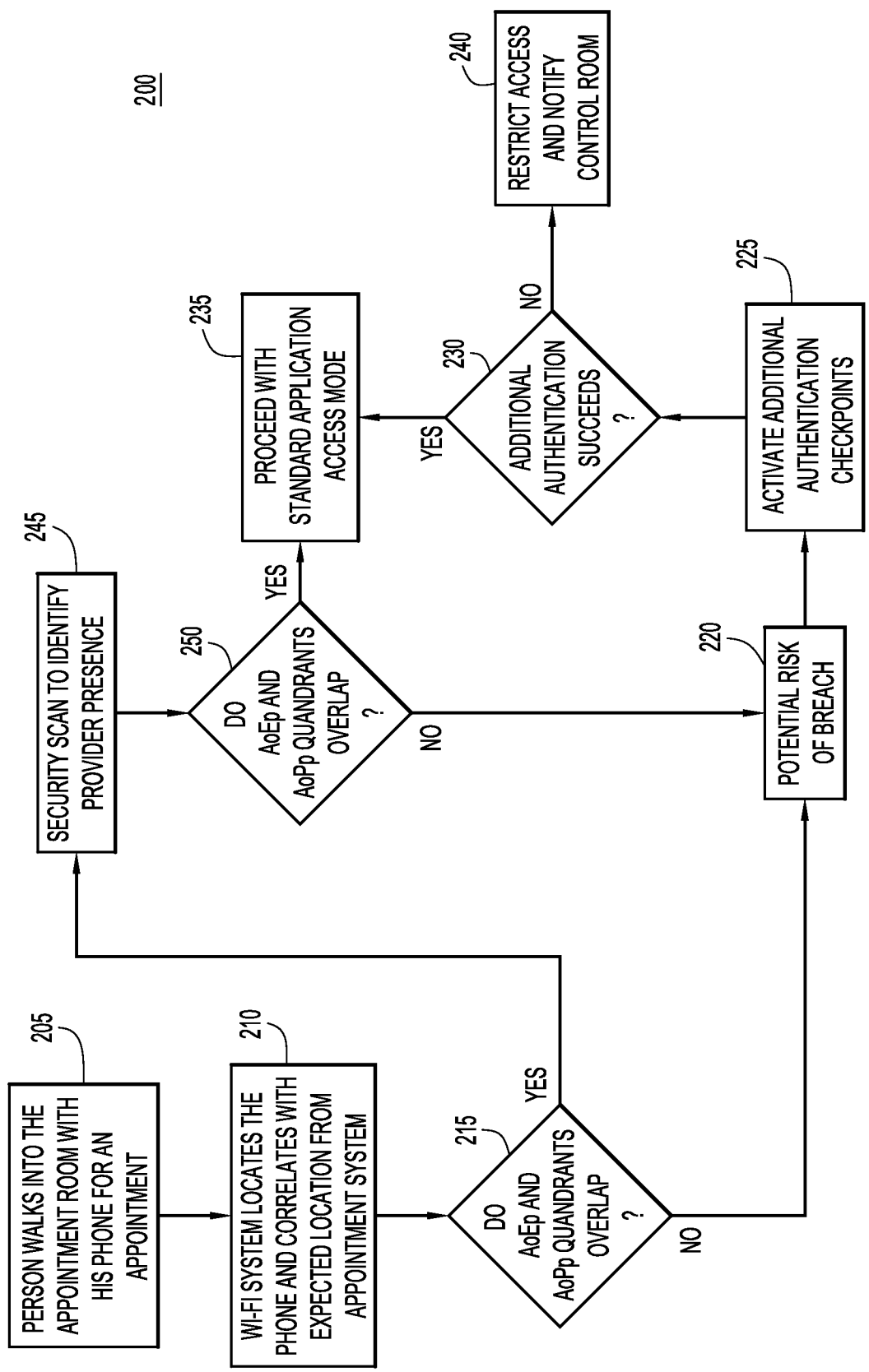
FIG. 2 is a flowchart illustrating a process for using time and motion data sets to detect and prevent unwanted participants in telehealth collaborative sessions based on physical presence determinations, according to an example embodiment.

With reference now made to FIG. 2, depicted therein is a detailed flowchart 200 illustrating how a process like that of flowchart 100 of FIG. 1 may be applied in a system to ensure privacy during a collaborative session. The process of FIG. 2 may be particularly applicable to a telehealth collaborative session in which the patient has not previously met the healthcare provider. The telehealth collaborative session example may implement the techniques described herein due to the sensitive nature of remote video telehealth collaboration. Furthermore, given Health Insurance Portability and Accountability Act (HIPAA) compliance considerations, and as telehealth becomes more prevalent, a perimeter-based, single data source approach to authentication may not ensure privacy. Accordingly, as will be described with reference to FIG. 2, multiple data sources and time and motion models may be leveraged to ensure trust and remedy risk in telehealth collaborative sessions.

By implementing a process like that of FIG. 2, an added level of trust is added to the collaborative session, leading to a more productive collaborative session. For example, in a typical telehealth collaborative session, a patient is sent a link to join the session, but may not know the doctor in advance. A person other than the healthcare provider may intercept the link to the session and attempt to participate in the session. As the patient has not previously met the healthcare provider, the patient may provide sensitive, private data to someone other than the healthcare provider, or the patient may be concerned that they are providing sensitive and/or private information to someone other than the healthcare provider. These are valid concerns in the healthcare field, an industry that tends to report a high number of sensitive information data breaches. By implementing a process like that of FIG. 2, data breaches may be prevented, and patients may participate in telehealth sessions with a higher level of trust, leading to more successful collaborative sessions.

The process of flowchart 200 creates a channel of trust verification for a telehealth remote video collaboration session using data sources from a facility's existing information technology infrastructure, as well as other information systems. Specifically, areas of presence (i.e., where a possible participant is located) in a room are evaluated in real-time using Wi-Fi location data to determine whether there are any possible trust or security breach issues. The process of flowchart 200 defines the following areas:

Areas of Expected presence (AoEp)—these areas are areas in which the telehealth collaborative session participants are expected to be located during the session.

Area of Actual presence (AoAp)—these areas are areas in which the telehealth collaborative session participants are determined to be actually located.

Area of Probable presence (AoPp)—these are areas similar to those of AoAp, but AoPps have determined presence to a lower level of precision than AoAps. For example, video shot data analyzed and mapped to a particular person may allow determination of an AoAp, as the actual person may be identified from the data. Similarly, voice recognition data may be a source of an AoAp as the actual participant may be identified from the data. On the other hand, Wi-Fi data from a voice over Internet Protocol (VoIP) phone may only be able to determine an AoPp as the user of the phone is more difficult to determine from Wi-Fi data than it is from video data.

Area of Unexpected presence (AoUp)—these areas are areas in which the telehealth collaborative session participants are not expected to be located during the session.

Once defined, these areas are evaluated for presence, and may be used to determine if an unexpected or unauthorized participant has joined the telehealth collaborative session. Specifically, an Intruder Risk Probability is created by mapping AoEps, AoAps, AoPps and AoUps together. A risk level for the collaborative session is determined from the overlap of the areas. This risk level may then be compared to, for example, a predetermined threshold risk level.

According to one example, the risk level may be determined as follows:

$$\text{Risk Level} = \text{location overlap of AoEp and AoAp with dilution of AoPp and AoUp}$$

The process flow for calculating this risk level begins in operation 205 of flowchart 200, when a user enters an appointment room for a telehealth collaborative session. The user may be the patient or the healthcare provider. The user may bring his or her own device with which to join the telehealth collaborative session, such as a smartphone, a tablet, or another portable computing device. According to other examples, the appointment room may be provided with devices that will allow the user to join the telehealth collaborative session.

In operation 210, the location of the device used to join the telehealth collaborative session is located. For example, a Wi-Fi signal through which the device connects to the Internet may be used to locate the device. According to other examples, energy usage for the device used to connect to the telehealth collaborative session may be used to determine where the user is accessing the telehealth collaborative session. This location is used to determine an AoPp for the participant. In the Wi-Fi example, the AoPp for the user may be the area that corresponds to the location for the user determined from the Wi-Fi signal strengths. As the location determined from the Wi-Fi signal strengths may not be exact, the AoPp may be an area in which a probability that the participant is located there is above a pre-determined threshold. In the energy consumption example, the AoPp may be an area surrounding an energy source, such as a predetermined distance from an electrical socket. Once determined, the AoPp is correlated with the expected location of the user from an appointment system. In other words, the AoEp for the participant is compared with the AoAp or AoPp for the user.

If it is determined in operation 215 that there is no overlap between the AoEp and the AoPp, the processing moves to operation 220 where the determination is made that there is risk of a breach of trust and/or security. In other words, if it can be clearly determined that one of the participants in the telehealth collaborative session is outside of where they are expected to be (i.e., there is no overlap between the AoEp and the AoPp), there is risk that the participant in the telehealth collaborative session is someone other than the invited participants, i.e., someone other than the patient or the healthcare provider. In response to the potential risk, potential breach of trust or potential breach of security, an additional authentication checkpoint is activated in operation 225. The additional security checkpoint may include requiring the participant to provide an employee identification password or number, and/or requiring the participant to scan a security badge. Other additional security checkpoints may include biometric security measures, such as retinal or fingerprint scans. The choice of the form of the additional security checkpoint may be based on the sensitivity of the information to be shared during the collaborative session and/or the potential risk associated with allowing an uninvited participant to access the collaborative session. These additional checkpoints allow for the verification of the participants in the telehealth collaborative session. If the participant successfully authenticates through the additional checkpoint in operation 230, the participant is allowed to enter the telehealth collaborative session in operation 235. On the other hand, if the participant fails to successfully authenticate at the additional authentication checkpoints, the participant's access to the telehealth collaborative session is restricted, and an authority, such as a control room, is notified in operation 240.

Returning to operation 215, if it is determined that the AoEp and AoPp do overlap, i.e., if the area where the participant is expected to be located overlaps with the area where the participant is determined to likely be located from, e.g., Wi-Fi or energy consumption data, the processing proceeds to operation 245 where an additional scan is performed to determine actual presence of a particular meeting participant. In other words, in operation 245 an AoAp is determined for the participant. If it is determined in operation 250 that the AoAp, the area in which the expected participant is actually located, overlaps with the AoEp, the area in which the expected participant is expected to be located for the telehealth collaborative session, then the participant is allowed to participate in the telehealth collaborative session. On the other hand, if the AoEp and AoAp do not overlap, the processing proceeds to operation 220, and continues as described above.

In summary, the process of flowchart 200 describes a process by which the location of a participant is determined based on an indication, such as Wi-Fi and/or energy usage data. This location may not be exact or may not specifically identify the individual associated with the access. If this area of possible presence overlaps with the area where the participant is expected to access the telehealth collaborative session, then additional steps are taken to actually verify that the participant is the correct participant for participation in the session. On the other hand, if the area of possible presence does not overlap with the area of expected presence, the participant is required to prove their identity before access to the telehealth collaborative session is permitted.

Figure 3:
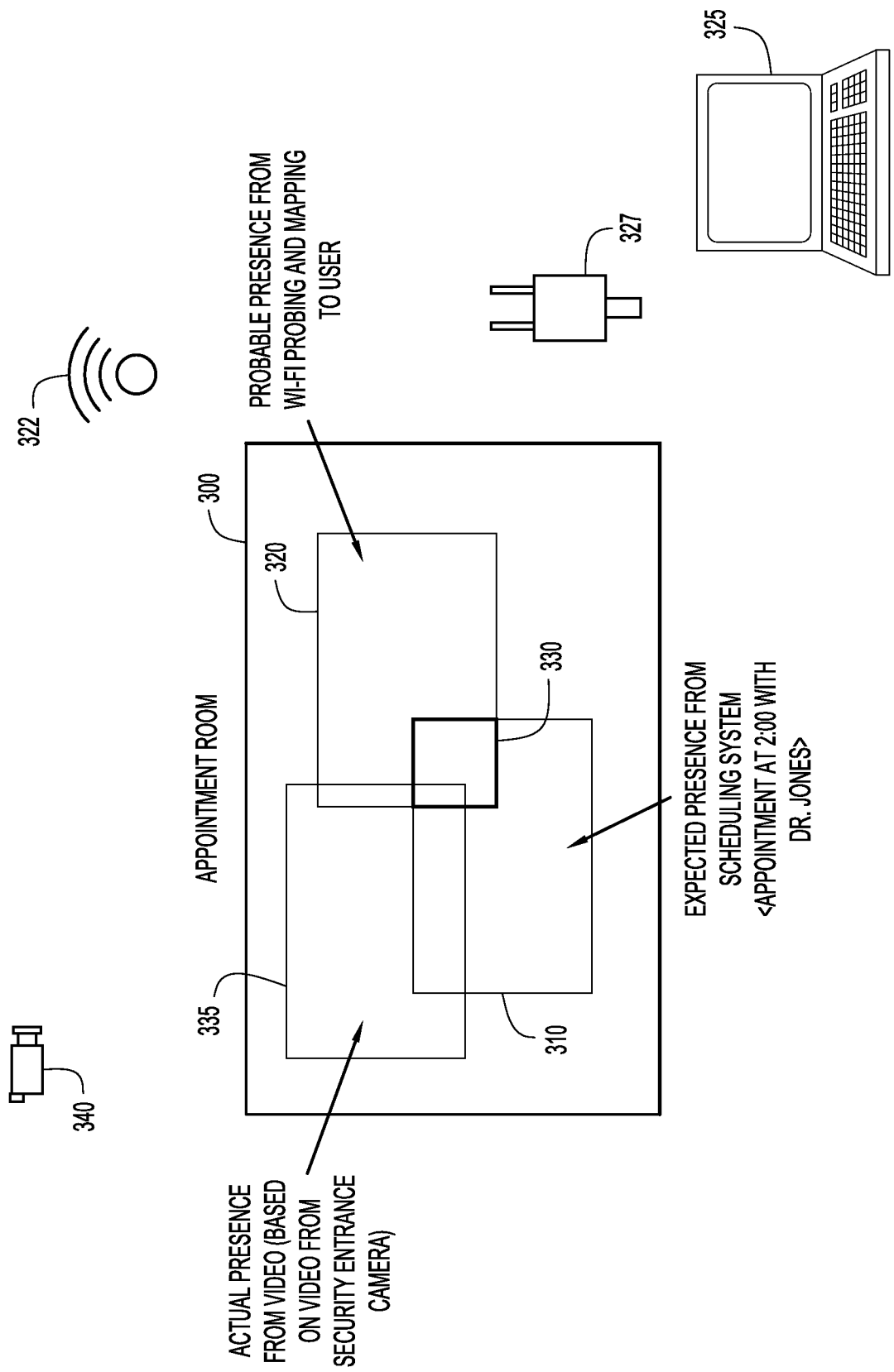
FIG. 3 is an illustration of a first example appointment room used for telehealth collaborative sessions that includes areas of calculated physical presence in order to prevent unwanted participants in telehealth collaborative sessions, according to an example embodiment.

With reference now made to FIG. 3, depicted therein is an example illustration of an AoPp, an AoEp and an AoAp that would follow operations 245 and 250 of FIG. 2. Specifically, depicted in FIG. 3 is an appointment room 300. A telehealth collaborative session is scheduled for a particular time and a healthcare provider is expected to participate in the session from appointment room 300. More specifically, it is expected that the healthcare provider will participate in the session at an area of appointment room 300 that is designed for use in telehealth collaborative session. This area is illustrated through area 310, and serves as an AoEp for the healthcare provider's participation in the telehealth collaborative session. When the healthcare provider attempts to the join the telehealth collaborative session, a Wi-Fi connection used to access the network over which the telehealth collaborative session will take place indicates an AoPp 320 for the participant. For example, Wi-Fi access point 322 may send Wi-Fi data to presence detection device 325. Based on this data, presence detection device 325 may determine AoPp 320 for the participant. Similarly, based on the energy usage of a device used to access the telehealth collaborative session, the AoPp 320 may be determined for the user. Accordingly, energy usage sensor 327 may send energy usage data to presence detection device 325, via which presence detection device 325 determines AoPp 320.

Because AoEp 310 and AoPp 320 overlap in area 330, it may be determined that the participant attempting to access the telehealth collaborative session is where they are expected to be when participating in a telehealth collaborative session, and therefore, the participant is not immediately blocked from participating in the session. Accordingly, as in operation 245 of FIG. 2, a scan is performed to determine the AoAp for the participant. According to the example of FIG. 3, a video scan of appointment room 300 is performed by video camera 340. Video camera 340 sends video data to presence detection device 325, and presence detection device determines the AoAp 335 for the participant. According to the example of FIG. 3, facial recognition performed by presence detection device 325 determines both the AoAp 335 and identity of the participant. Finally, because AoAp 335 overlaps with AoEp 310 (and also AoPp 320) the participant is allowed to participate in the telehealth collaborative session.

As further illustrated in FIG. 3, the processes and systems described herein leverage data sources, such as Wi-Fi access point 322, video camera 340 and energy data source 327 that are already incorporated into the IT infrastructure of the provider of appointment room 300. Furthermore, presence detection device 325 may be incorporated in, or connected to, the scheduling systems that healthcare providers already use to schedule telehealth and traditional appointments. Accordingly, the systems and processes described herein may be implemented by telehealth collaborative sessions without making new capital expenditures. Also as illustrated in FIG. 3, profiles, including the AoAp, AoEp, AoPp and AoUp, of who should be where for a telehealth collaborative session may be used to ensure trust. The time and motion data sets employed in the systems and processes described herein may provide a correlated view of the environment that improves upon a binary decision provided by a personal identification system. In other words, the systems and processes described herein leverage the context of a telehealth collaborative session to enforce trust relationships.

Figure 4:
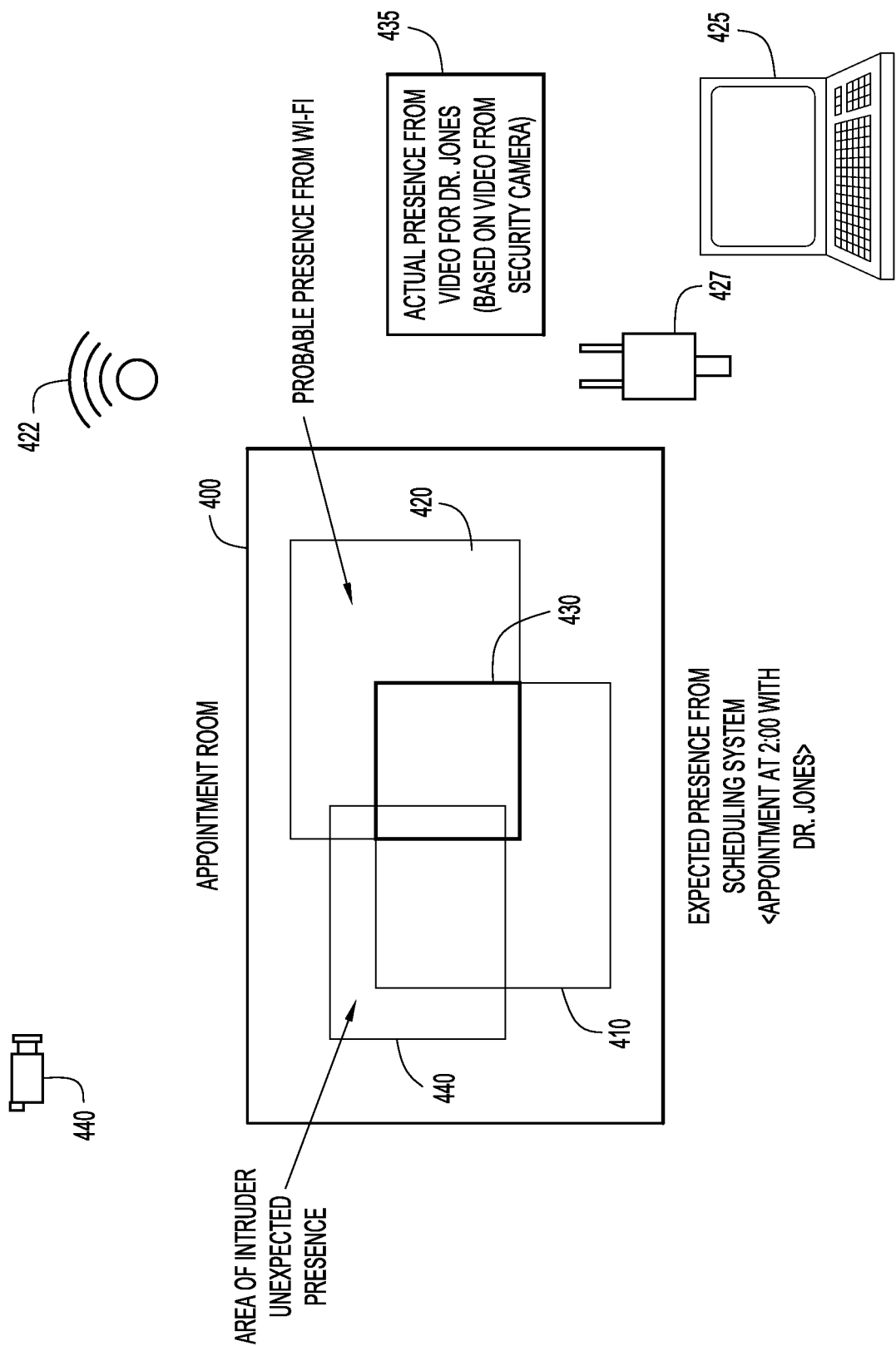
FIG. 4 is an illustration of a second example appointment room used for telehealth collaborative sessions that includes areas of calculated physical presence in order to prevent unwanted participants in telehealth collaborative sessions, according to an example embodiment.

With reference now made to FIG. 4, depicted therein is an example that illustrates the processing that takes place when an unauthorized participant (i.e., someone other than the healthcare provider or the patient) attempts to access a telehealth collaborative session. In other words, FIG. 4 illustrates an example to which the processing of operations 245, 250, 220, 225, 230 and 240 of FIG. 2 are applied.

Similar to FIG. 3, illustrated in FIG. 4 are an appointment room 400, a Wi-Fi access point 422, an energy consumption sensor 427, a video camera 420, and a presence detection device 425. Instead of an authorized participant attempting to access the telehealth collaborative session, an intruder enters appointment room 400 and attempts to access the telehealth collaborative session. It is expected that the healthcare provider will participate in the session at an area of appointment room 400 that is designed for use in telehealth collaborative sessions. This area is illustrated through area 410, and serves as an AoEp for the healthcare provider's participation in the telehealth collaborative session. When the intruder attempts to the join the telehealth collaborative session, a Wi-Fi connection used to access the network over which the telehealth collaborative session will take place indicates an AoPp 420 for the participant. For example, Wi-Fi access point 422 may send Wi-Fi data to presence detection device 425. Based on this data, presence detection device 425 may determine AoPp 420 for the participant/intruder. Similarly, based on the energy usage of a device used to access the telehealth collaborative session, the AoPp 420 may be determined for the participant/intruder. Accordingly, energy usage sensor 427 may send energy usage data to presence detection device 425, via which presence detection device 425 determines AoPp 420.

Because AoPp 420 overlaps with AoEp 410 through area 430, the intruder is not immediately denied access to the telehealth collaborative session. Instead, a scan is performed to determine the AoAp for the participant. According to the example of FIG. 4, a video scan of appointment room 400 and the surrounding area is performed by video camera 440. Video camera 440 sends video data to presence detection device 425, and presence detection device 425 determines AoAp 435 for the actual participant in the telehealth collaborative session. According to the example of FIG. 4, facial recognition performed by presence detection device 425 determines both the AoAp 435 for the intended participant. Specifically, facial recognition is used to specifically identify the doctor who is expected to be participating in the collaborative session. Furthermore, the presence identified as being located within AoUp 440 may be determined to be an In other words, because AoUp 440 does not overlap with AoAp 435 nor does it overlap with AoEp 410, the intruder is not provided access to the telehealth collaborative session. Furthermore, because the AoAp 435 does overlap with AoPp 420, it may be determined that it is the intruder that is attempting to access the telehealth collaborative session, as AoUp 440 does overlap with AoPp 420. In response to these determinations additional authentication checkpoints are required of the intruder, as described above with reference to operation 225 of FIG. 2. If the intruder fails the checkpoints, the intruder is denied access to the telehealth collaborative session.

Accordingly, as illustrated through FIGS. 2-4, a system and process are provided in which:

Secondary channels based on existing IT infrastructure and other information systems may be leverage for identifying trust levels for a remote video collaborative session.

Multiple data sources are correlated to derive AoEps, AoAps, AoPps and AoUps.

Intruder risk probability may be determined based on overlap of AoEps, AoAps AoPps and AoUps.

Zone based modeling may be used to view current trust zones and overlap to understand the level of intruder risk probability along with loss prevention events.

False positive identifications of intruders may be eliminated by prompting potential intruders to authenticate using another form of authentication Trust models using additional data sources to layer on top of existing application security/privacy models are provided.

Derived trust quadrants may be mapped with expected boundaries.

Furthermore, while described above within the context of a telehealth scenario, the techniques described herein may be broadened to, for example, any online-collaborative session and/or online meeting session. These systems ensure authenticity of participants in privacy and security sensitive video health consultations, provide compliance with applicable privacy laws and expectations, and implement multi-channel verification of participants.

Figure 5:
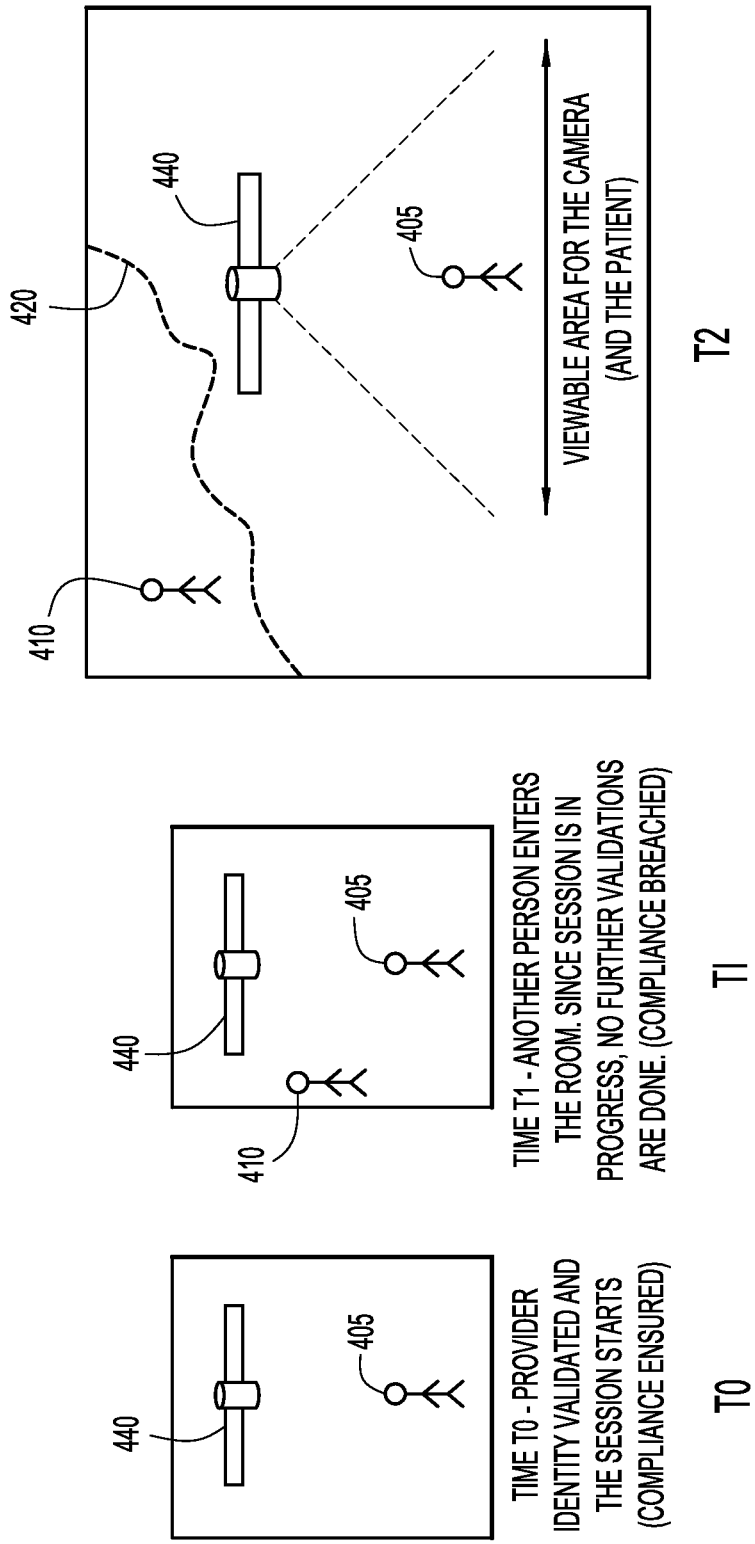
FIG. 5 is an illustration of continuous and passive authentication of participants in telehealth collaborative sessions made possible through correlation of multiple time and motion data sets, according to an example embodiment.

With reference now made to FIG. 5, depicted therein are additional intruder detection scenarios to which the systems and processes of FIGS. 2-4 may be applied. Illustrated in FIG. 5 are three times during a telehealth collaborative session, time T0, time T1 and time T2. At time T0, participant 405 joins the telehealth collaborative session through the processes described above with reference to FIGS. 2-4. In addition to the trust establishment procedures of FIGS. 2-4, the systems processes described herein may also provide continuous monitoring of participants, or intruders to a telehealth collaborative session, thereby ensuring that trust is maintained throughout a telehealth collaborative session. As illustrated at time T2, subsequent to participant 405 joining the telehealth collaborative session, a possible intruder 410 enters the vicinity of where participant 405 is participating in the telehealth collaborative session. The presence of intruder 410 may be detected through the same means described above that were used to determine AoAps, AoEps, AoPps and AoUps. If the presence detected for intruder 410 overlaps with one or more of the AoAps, AoEps, or AoPps for participant 405, it may determined that intruder 410 is possibly overhearing or otherwise intruding on the telehealth collaborative session. Accordingly, participant 405 or some authority, such as a control center, may be notified that there is a possible intruder in the telehealth collaborative session.

Also illustrated in FIG. 5 is T2. At time T2 a possible intruder may be detected even if intruder 410 is hidden or otherwise obscured from the view of participant 405 and/or video camera 440. Specifically, screen 420 blocks intruder 410 from the view of both participant 405 and camera 440. Because the systems and processes described herein correlate multiple data sources, such as Wi-Fi and energy data, the presence of intruder 410 in an area that overlaps with the AoAp, AoEp, or AoPp for participant 405 may be detected.

Similar to the discussion above regarding continuous intruder detection is the passive authentication provided by the systems and processes described herein. Some other systems require the user to actively engage with a device in order to authenticate to a telehealth collaborative session. Asking participants to actively engage in the authentication is time consuming. On the other hand, as illustrated in operations 205, 210, 215, 245, 250 and 235 of FIG. 2, a user may be authenticated to a telehealth collaborative session without asking the participant to actively engage in any authentication procedures. Furthermore, the passive, continuous authentication described above provides additional security over that provided by systems that utilize badge or even biometric authentication techniques like iris scans. For example, the techniques described herein utilize multiple independent (out of band) data sources, that when combined ensure that risks are timely identified. The techniques described herein combine multiview verification and behavior based verification that is independent of the telehealth collaborative session hardware and software utilized to provide the collaborative session. In other words, as other authentication systems may be limited to perimeter and initial verification, the techniques described herein are better suited for ensuring continuous privacy in remote collaboration based telehealth.

Finally, the techniques and processes described herein may be implemented in response to HIPAA concerns. Environments that may be subject to HIPAA requirements do not have uniformity in design, security, and operating conditions. In fact, telehealth will become more and prevalent, and will be implemented in environments other than hospitals, such as field clinics, elderly housing, and even homes. Because the systems described herein leverage existing IT infrastructure, the techniques may be implemented without requiring specialized hardware and/or sensors.

Figure 6:
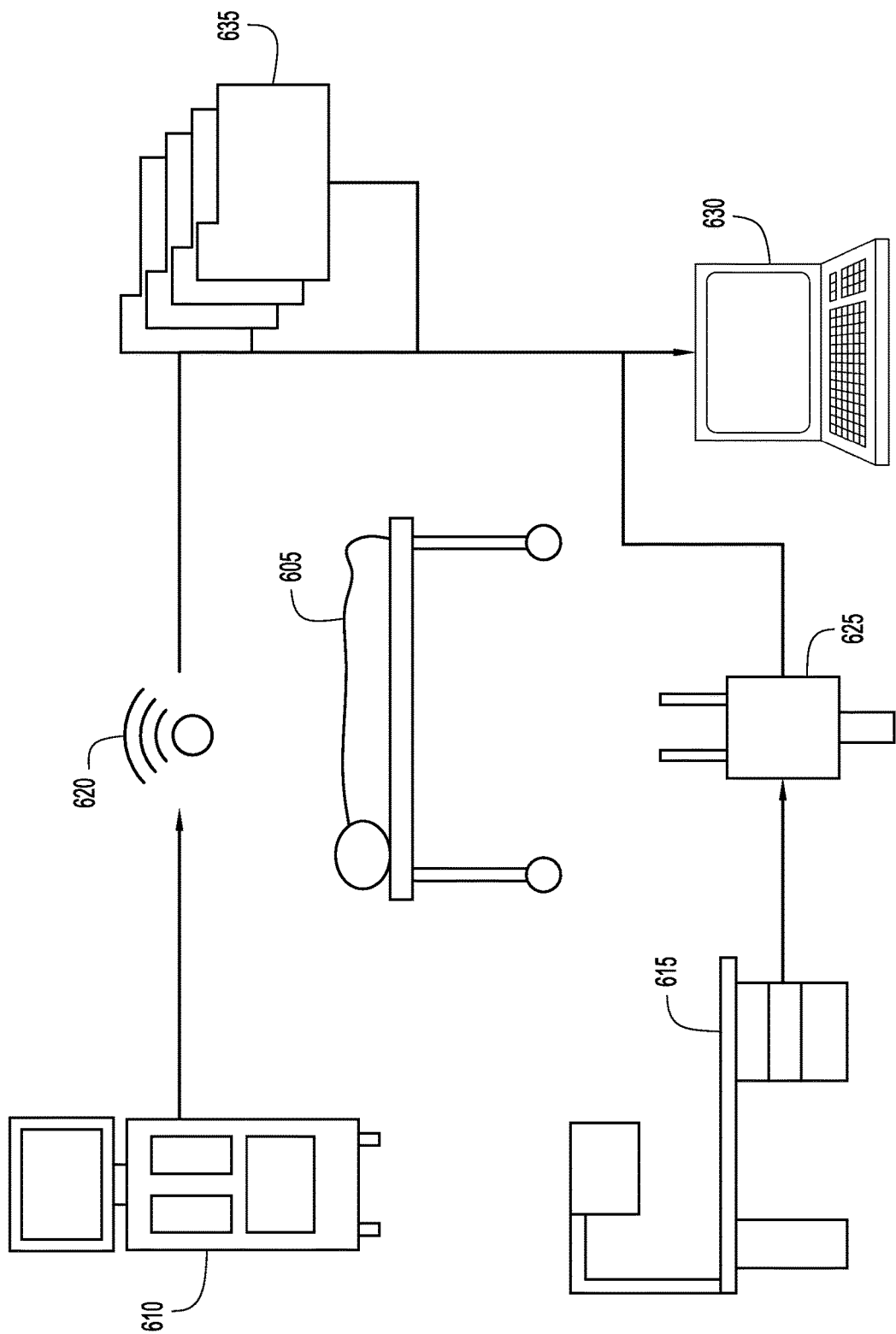
FIG. 6 is an illustration of using multiple time and motion data sets to determine the physical presence of medical devices, according to an example embodiment.

With reference now made to FIG. 6, depicted therein is another application of the process of FIG. 1. Illustrated in FIG. 6 is a patient 605 that is being monitored by medical devices 610 and 615. In many cases, these pieces of equipment are not mapped to logical entities (such as patient 605) or to key medial processes (such as billing). By applying the techniques described herein to medical environments like that of FIG. 6, equipment may be mapped to medical logical entities and to medical electronic processes. For example, applying the techniques described herein to the environment illustrated in FIG. 6, relationships between patient 605 and medical devices 610 and 615 may be mapped. This mapping may be used to verify and/or remedy issues in medical billing records.

Specifically, data indicating that medical device 610 has monitored patient 605 is sent to medical record and billing verification device 630 through Wi-Fi access point 620, while data indicating that medical device 615 is monitoring patient 605 is sent to medical record and billing verification device 630 based on location information provided by energy consumption data source 625. Furthermore, multiple data sources may be used to confirm that medical equipment 610 and 615 have been used to monitor patient 605. For example, the Wi-Fi data and energy consumption data may be correlated to confirm that a particular device is monitoring a particular patient. Similarly, video data or radio frequency identification (RFID) data may also be correlated with other data sources to determine which medical equipment is or has monitored a particular patient. This correlation of multiple data sources may take place via medical record and billing verification device 630.

Once there is a mapping between patient 605 and medical equipment 610 and 615, the mapping may be compared to an industry accepted mapping of medical billing codes to medical devices stored in a memory of medical record and billing verification device 630. By combining these two mappings, when an administrator enters a billing code into a billing system, medical record and billing verification device 630 may check which medical devices were present in the patient space at the time of the visit/procedure/stay. The medical record and billing verification device 630 then compares the devices present in the patient space to the expected devices for the billing code. If a mismatch is found, the administrator is alerted, and the mismatch may be remedied. Similarly, before being sent out to patients, electronic content of medical billing records 635 for patient 605 may be compared with which medical devices that were present in the space associated with patient 605 at the time of the visit/procedure/stay that is being billed. If there is a mismatch between the billing information 635 and the mappings stored in medical record and billing verification device 630, the mismatch will be identified and remedied by medical record and billing verification device 630.

Figure 7:
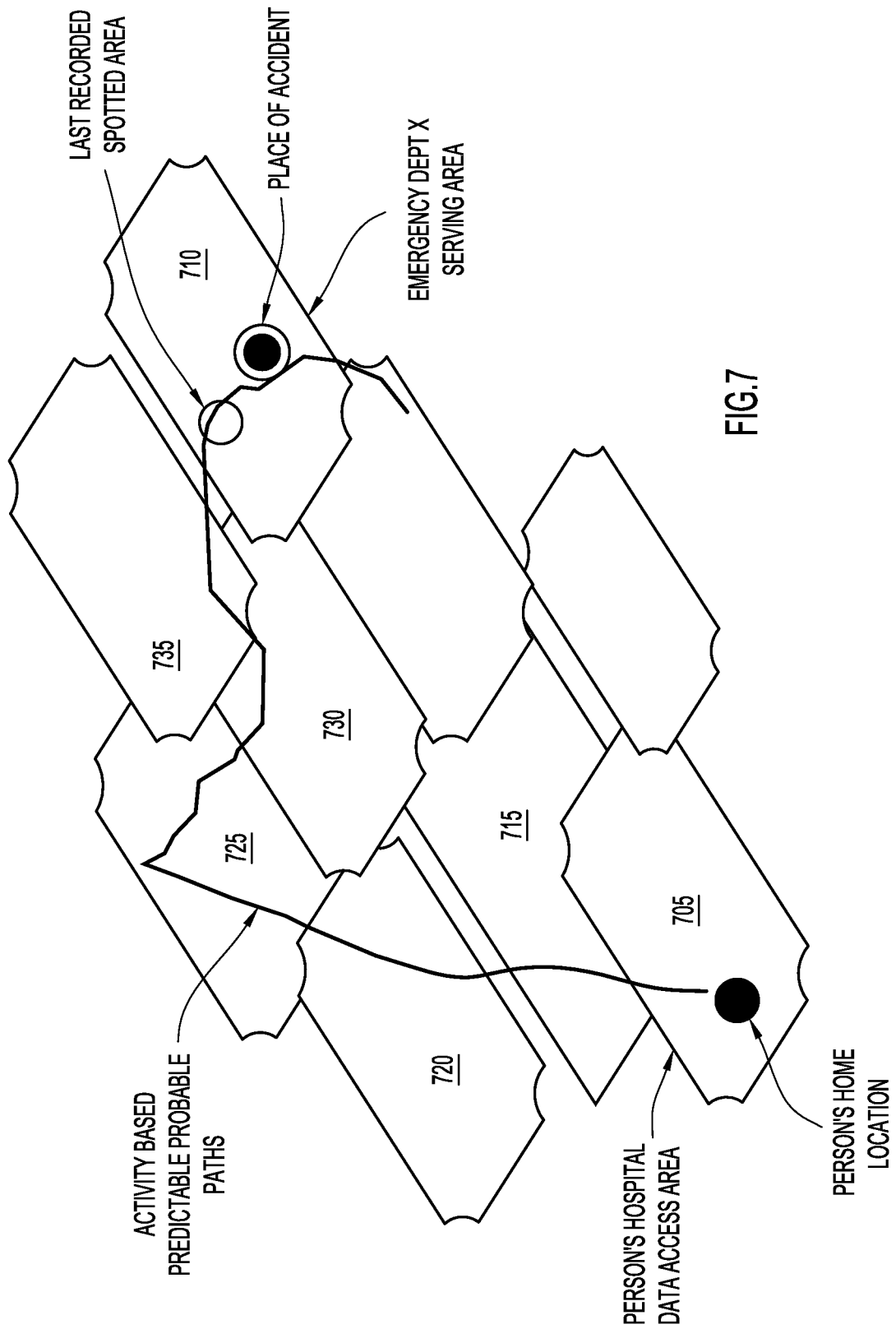
FIG. 7 is an illustration of tracking physical presence of a person, and forwarding electronic medical record information for the person, through the use of multiple time and motion data sets, according to an example embodiment.

With reference now made to FIG. 7, depicted therein is an example environment in which the techniques described herein make critical emergency electronic medical record information available at points of care as a patient is moved from, for example, the location of an emergency event to a location where additional care is provided regardless of where the emergency took place.

Absent the techniques described herein, when an emergency happens outside of a hospital, medical facility, or far from a patient's home, the responding medical personnel rarely have critical information about the patients. Nevertheless, the availability of this information is critical, can be lifesaving, can avoid complications and can prevent wasteful additional tests (i.e., test results in the medical records may not need to be performed again if the information was available to the emergency responders). Access to medical records allows responders to make faster decisions, and decisions that are more likely to be correct.

Illustrated in FIG. 7 is a process that uses time and motion models to provide a parallel channel approach that provides critical information to emergency personal, without opening up electronic medical records (EMR) to public access. In other words, the system identifies a problem (i.e., an emergency situation) through time and motion data and models, and takes steps to remedy the problem by providing the EMRs to the location where they are needed.

In FIG. 7, a person whose "home" area, i.e., the area where an individual lives or works, and where that that individuals EMRs are likely located, is indicated via reference numeral 705. Within home area 705 is a primary care provider (PCP) network that can access data from its branches, including access to EMR data. Once the patient crosses the boundary of area 705, EMR data for the patient may not be immediately accessible in the area in which the patient is located. Area 710 is where the person experiences a medical emergency. Because area 710 is not the person's home area, i.e., not area 705, EMR data for the person may not be immediately available within area 710. By applying the techniques described herein, the EMR data stored and accessible in area 705 is made available to area 710.

The EMR data is made available to area 710 based on the movement, activity or location of the person. Concise critical data follows the person as the person moves through areas 715, 720, 725, 730, 735, and 710. The concise critical data is transferred using a parallel channel created by a network at the fog layer. A network blade in a router may be used to store such data. The data is transient and is not stored permanently in the router. Using a network-based model leveraging a healthcare emergency data blade in the router in the first responder/ER network, the emergency information can be mined from the network of the closest fog routers using available attributes even if key information such as a medical record number (MRN) is not available. The closest fog routers are identified by contextual information such as location and activity. The emergency critical data is made available at the network node blades by an intelligent system that is able to generate a personal critical medical information package (PCMIP) from medical information of the patient.

Accordingly, in home area 705, a PCMIP is created for the person. The PCMIP may be automatically created from the person's EMR data, or a medical professional, such as a physician, may create a PCMIP. Also included in the PCMIP may be multiple identification elements such as biometrics (e.g., an iris scans). Based on the activity of the person (e.g., a gate location at airport is identified or data indicating the user has booked a flight to a particular destination) the system starts to predict the path of the person. The path of a person may also be predicted based on, for example, Wi-Fi and/or energy consumption data gathered from devices used by the person. Based on the predicted path, the PCMIP is transferred to the secure router blade on the emergency management system network (EMSN) for the duration of the person's path prediction. Accordingly, in FIG. 7, as the person moves from area 705 to 715, the PCMIP for the person is automatically transferred to the fog router in location 715. Similarly, the PCMIP will follow the person as the person moves to locations 720, 725, 730, 735, and 710. The PCMIP is intelligently distributed to a set of fog routers near the patient's current location. The patient's location is determined based on a predicted path, which is derived by analytics using activity data sources. The zones are modeled based on the emergency responding territories to avoid proliferation of data storage, yet providing sufficient parallel access to ensure that the PCMIP will be available when needed. Accordingly, the EMR data is transferred to area 710 in response to context and derived insights.

When the emergency takes place in area 710, the person's PCMIP is now accessible in area 710, assuming it is unlocked through the procedure to be described below with reference to FIG. 9. The PCMIP may be accessible to hospitals and other medical facilities located in area 710. Similarly, the PCMIP may be accessible to first responders and other emergency personnel who travel to the location of the emergency.

Figure 8:
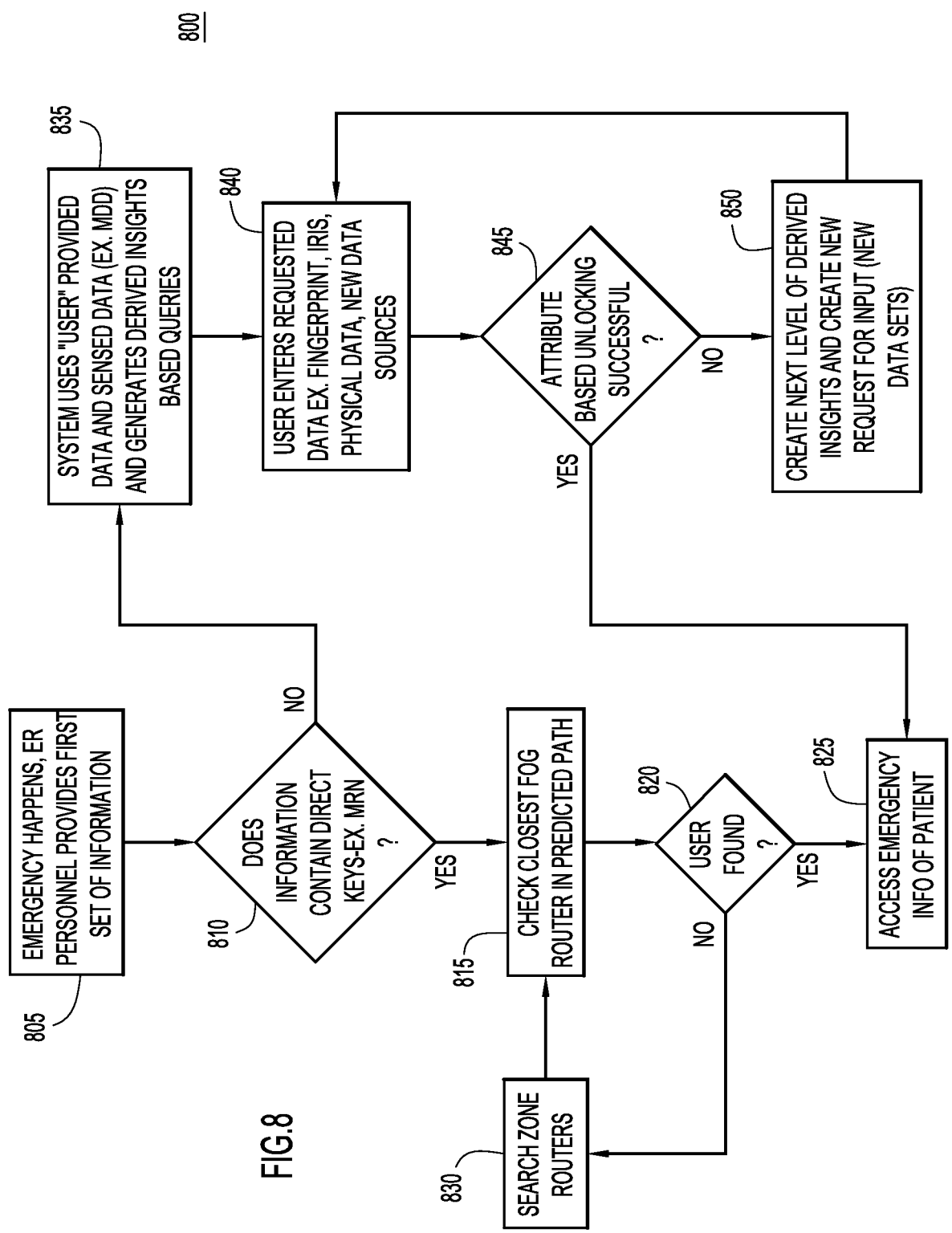
FIG. 8 is a flowchart illustrating a process for tracking the physical presence of a person, and forwarding electronic medical record information for the person, through the use of multiple time and motion data sets, according to an example embodiment.

With reference now made to FIG. 8, depicted therein is a flowchart 800 illustrating a process for making EMR data, such as a PCMIP, available as a user moves from their home location to another location. The process begins in 805 when an emergency takes place. During operation 805, the first responders and/or other medical personnel provide information that will be used to access the EMR data for the person who experienced the emergency.

In operation 810, it is determined whether or not the information provided in 805 contains a direct key to the EMR data, such as a MRN. If a direct key is provided, the closest fog router to the location of the emergency is checked in operation 815. It is determined in 820 whether or not the fog router contains the EMR data indicated by the key. If the EMR data is in the fog router, access is granted to the EMR data. On the other hand, if the fog router does not contain the data, routers along the person's predicted path are searched in reverse order in operation 830. Operations 815, 820 and 830 will loop until the records associated with the key are found, and the processing moves to operation 825 where access is granted to the records.

On the other hand, if the information provided in operation 805 does not contain a direct key, the processing moves from operation 805 to 835 where, based on the information provided, the system generates derived insight based queries. Specifically, in operation 835, the user is prompted to provide additional information that will identify the person experiencing the emergency. The prompts will be based on derived insights. In operation 840, the emergency responder or other individual attempting to access the EMR data provides responses to the prompts. This information may include identifying data about the person experiencing the emergency, such as a retinal scan, a fingerprint scan, or other identifying physical data about the person experiencing the emergency. In operation 845 it is determined whether or not a successful unlocking of the EMR data has taken place (which will be described below with reference to FIG. 9). If the unlocking is successful, access to the EMR data is provided in operation 825. On the other hand, if the unlocking is unsuccessful, next level derived insights will be generated and used to create new prompts for the person attempting to access the EMR data. Operations 840, 845 and 850 will loop until a successful unlocking takes place.

The unlocking process discussed in operation 845 of FIG. 8 will now be described with greater detail, and with reference to FIG. 9. As discussed above, when an accident occurs, a medical professional may attempt to access EMR data for a patient. The medical professional will be prompted to provide identifying information about the patient, such as an iris scan, a finger print scan, a description of identifying characteristics about the patient such as identifying marks (tattoos, moles, etc.) or physical characteristics, such as height, weight, hair color, and eye color, among others. The medical professional may also be prompted to provide additional information, such as location information.

The system on the other end, i.e. a device configured to provide access to EMR data, validates the information provided by the medical professional, and based on the context (e.g., a probability that the person could have been in the area) scans through the zones and identifies potential matches to the provided information. Based on results of the scans, additional prompts will be provided to the medical professional to narrow down the possible persons identified by the information provided by the medical professional. Once the information provided by the medical professional sufficiently identifies a person, the medical professional is validated, and the system provides access to the patient's EMR data.

The information that the medical professional is prompted to provide may include information that will distinguish the patient from other possible patients identified in the scans of the zones, as well as information that would only be known to the medical professional if the medical professional was actually providing care to the person. Furthermore, there may be multiple levels of unlocking to gain access to a patient's EMR data. The system scans the zones and the PCMIP to generate the relevant challenges. This model ensures the access controls are maintained and any access is logged.

Figure 9:
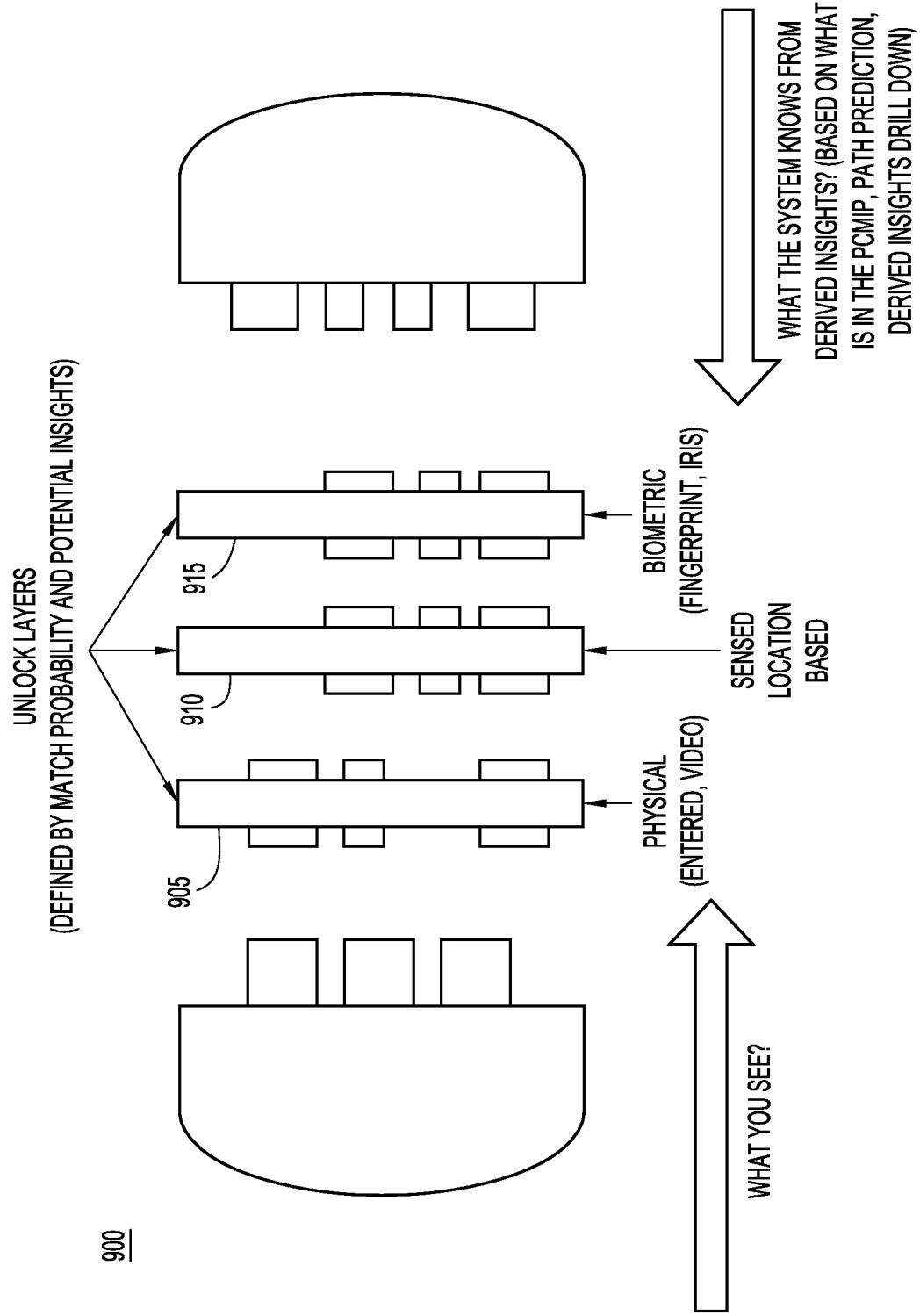
FIG. 9 is a graphical representation of the use of multiple levels of locking to ensure privacy of electronic medical record information, according to an example embodiment.

These multiple levels of locks are graphically illustrated in the "lock" 900 of FIG. 9 that includes lock levels 905, 910 and 915. As illustrated, unless in the information 920 provided by the person attempting to access the EMR data includes information for all three of lock levels 905, 910 and 915, the system 925 will not be unlocked.

The multiple locks can include levels such as
Physical appearance (height, marks)
Biometric (finger print, iris)
Special identification (marks verification)
Device identification (associated device, tags)

Figure 10:
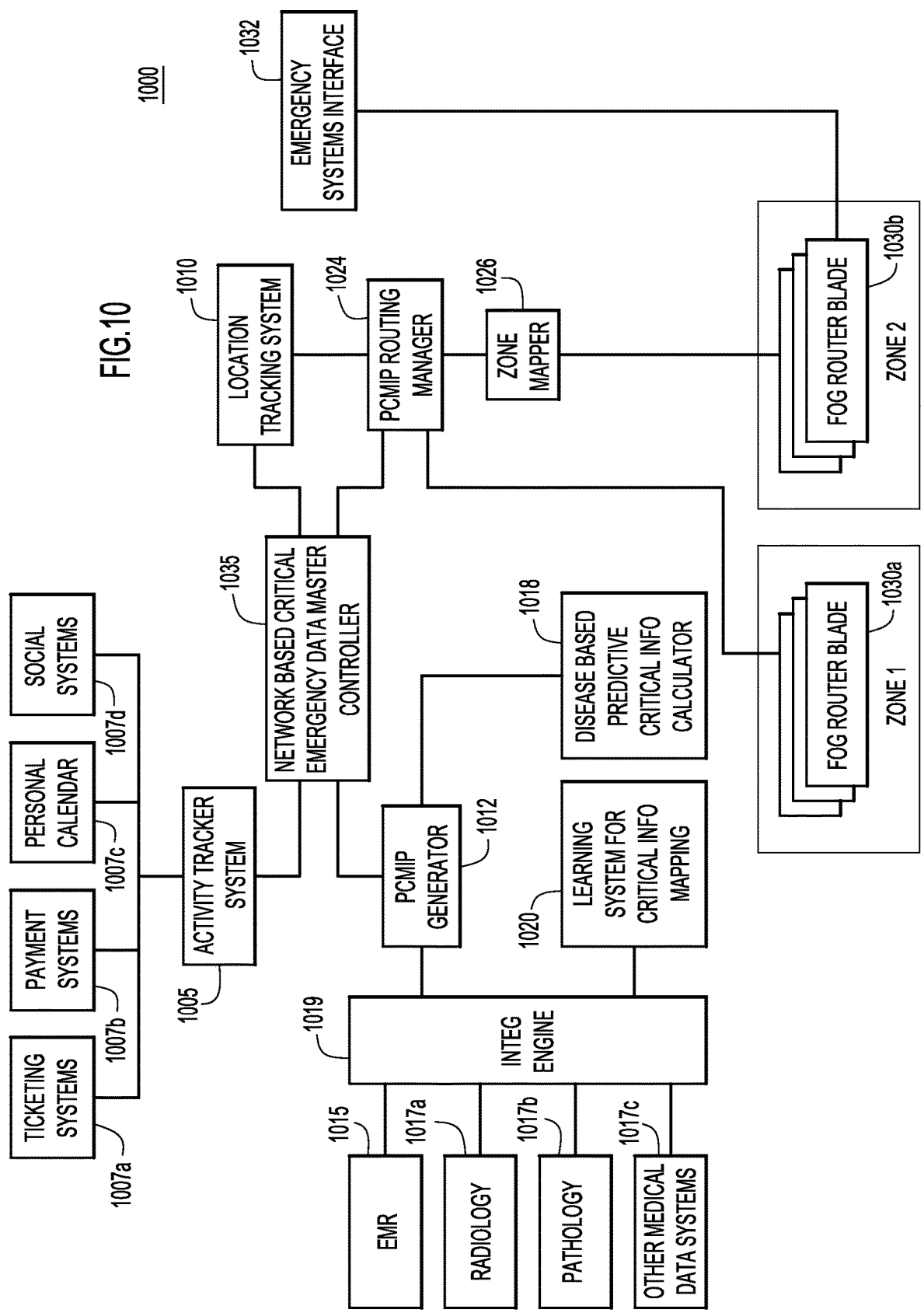
FIG. 10 is an illustration of a system configured to track individuals and forward electronic medical record information, according to an example embodiment.

In order to implement a system to carry out the features illustrated in FIGS. 7-9, the following functional components illustrated in system 1000 of FIG. 10 may be used:

Activity Tracker system 1005 tracks the user activity based on a range of data sources 1007*a-d* such as travel ticket database 1007*a*, payment systems database 1007*b*, a personal calendar 1007*c* and/or social networking information 1007*d*.

Location Tracker System 1010 tracks the location of the person. This tracking may leverage existing techniques like wireless location mapping, global positioning system data received from, for example, a smart phone.

PCMIP Generator 1012—operates in conjunction with the EMR system 1015, and other medical data sources 1017*a-c* and generates the PCMIP package with the most critical information about the patient. Integration engine 1019 may combine and organize the data from data sources 1015 and 1017*a-c* into a form that may be more easily accessed by PCMIP generator 1012. The generation of the PCMIP may vary from person to person depending on his or her special conditions. For example, for a person that has hypertension, the data retrieved from data sources 1015 and 1017*a-c* may be data specific to and/or related to the condition that is critical during an emergency. PCMIP generator 1012 may be embodied with intelligence to determine what information from data sources 1015 and 1017*a-c* may be useful for the patient in the case of an emergency. In order to determine which information is critical to an emergency, PCMIP generator 1012 may be able to access predictive critical information calculator 1018. Predictive critical information calculator 1018 may provide a calculation of which information should be retrieved for a particular disease and/or condition. Additionally, learning system 1020 may be provided to integration engine 1019 to allow integration engine 1019 to learn which information from data sources 1015 and 1017*a-c* are critical for the generation of a PCMIP.

PCMIP Routing Manager 1024 determines where to route the PCMIP and calculates the zone and the zone nodes that should be the destination for storing the PCMIP. Zone mapper 1026 may be accessed by PCMIP routing manager 1024 to determine the locations of the zones and zone nodes that are proximate to the patient's current location.

Fog router healthcare data container blades 1030 and b serve as a storage server for the PCMIP that is closest to the point of care for the patient that may be accessed in the case of emergency. Fog router healthcare data container blades 1030a and 1030b may be embodied as routers that include a data blade. Fog router healthcare container blades 1030a and 1030b may also be embodied as fog routers running an application enablement framework, such as Cisco's IOx™, and an "EmergencyTransientDataSystemNode" application in a secure Linux container.

Emergency system interface 1032 works in conjunction with an emergency response system such as an Emergency 911 system and knows to reach the closet fog router 1030a or 1030b and query for the patient's PCMIP based on available parameters, such an identifying number like a driver's license number or social security number, a patient's name, a patient's picture, a patient's physical dimension mapping, and others.

Network based critical emergency data master controller 1035 serves to manage the interconnections between activity tracker system 1005, location tracking system 1010, PCMIP generator 1012 and PCMIP routing manager 1024.

In other words, the operations of FIGS. 7-9 implemented in a system like that of FIG. 10 make critical EMR data available at points of care to emergency and other healthcare personnel in the event of an emergency or other medical situations outside of a patient's home area. Time and motion models provide a parallel channel approach that provides critical information to emergency personal, without opening up the EMR data to public access. The use of time and motion data enables the access to EMR data after multiple levels of validations are successfully performed. The parallel channel approach described above may provide critical information to emergency personnel, while avoiding making the EMR data publicly accessible, thereby avoiding privacy issues.

By implementing the operations of FIGS. 7-9 and/or the system of FIG. 10, the following advantages may be achieved:

When an emergency occurs, EMR data about the patient is readily available to the emergency personal.

Point of source availability of EMR data is provided even when a major disaster happens and a wide area network is out of service.

Increased speed of access to critical data is provided.

No manual transfer of the data is needed.

Automatic synchronization of the latest data is included in the PCMIP in response to changes in EMR data.

The PCMIP follows the person and ensures the data source closest to the person has the PCMIP data.

Encryption may be employed and the systems may implement a "no trace left behind" model for privacy and security.

A transient model is used and data times-out as a person moves from one location to another.

The systems and processes work with different EMR systems leveraging a universal standards based language.

Additionally, the systems and processes described with reference to FIGS. 7-10 address privacy concerns, and HIPAA concerns in particular. Accordingly, the systems and processes may include data opt-out options for users, allowing the user to opt out of the system at any time. Furthermore, before a patient's information is used in a system as described above, the patient may be required to explicitly opt-in to the system.

In emergency situations, scans of PCMIPs may not be subject to HIPAA concerns as emergency situations are considered "break the glass" situations. The systems and processes described above may also address HIPAA concerns for the storage and transfer of the data through the following procedures:

Physical safeguards—physical security is implemented at a healthcare data blade that is inserted and secured inside a router.

Technical safeguards—technical security is implemented using a transient data storage model that is encrypted and secured. The data may be stored in memory with options to save to disk for scalability. The servers may be designed to "swipe and rebuild" when a memory card is removed from the server.

Audit reports—clear audit procedures may be followed in the systems and methods of FIGS. 7-10, and access controls to the procedures may be enforced. For examples, shared key may be used between hospitals and emergency systems such as 911 centers, and access logs may be maintained.

Figure 11:
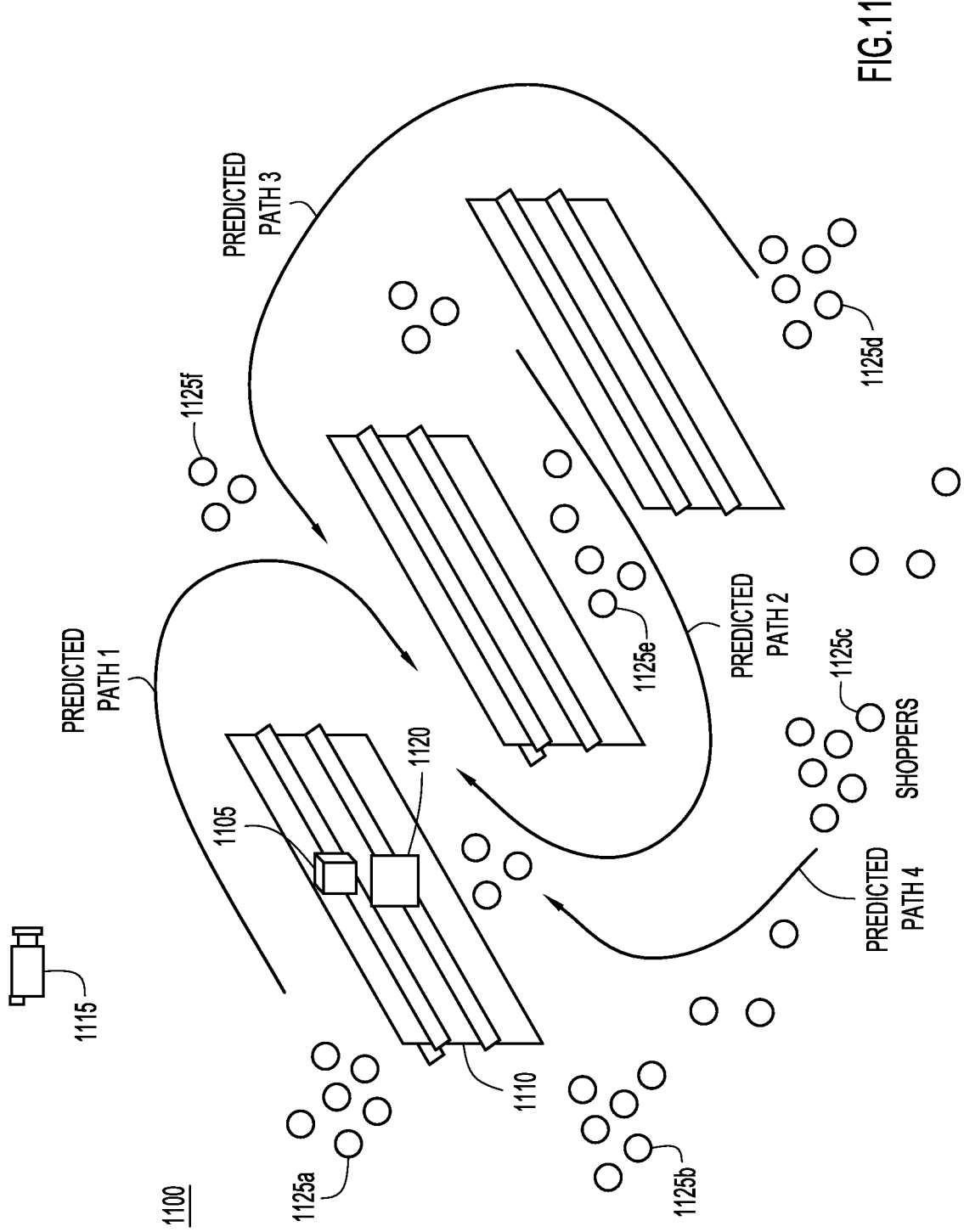
FIG. 11 is an illustration of a store environment configured to track the physical presence of products, according to an example embodiment.

With reference now made to FIG. 11, depicted therein is process by which a misplaced or wrongly positioned product may be identified and remedied using time and motion data, and in particular, multiple time and motion data sets. The techniques illustrated in FIG. 11 may be implemented to prevent misplaced products from presenting safety concerns in store aisles. For example, a large box on a higher shelf that is not positioned properly may be knocked down by a shopper or fall on the head of a shopper as they walk through the aisle. A spill is another example of a safety risk that may be addressed by the techniques described herein.

Multiple data sets and the derived insights are important in product heavy environments like stores for the following reasons:

The environments are dynamic in nature with frequent placement and layout changes. Using multiple sources such as inventory systems, video, and Wi-Fi data allows for the creation of an accurate analysis of the products.

Multiple data sources make the analysis of the products sufficiently accurate to avoid false positives while making the analysis sensitive enough to avoid missing products likely to fall. For example, two boxes stacked back to back, but protruding in the shelf might look like a perfect placement, but a second view of video can capture the variations that indicate one of the two products is likely to fall.

Multiple data sources allow for a stock time view of the products that reference layout and pressure vectors. In order to create a stock time view, data is used from stock tracking systems, Wi-Fi tracking of store personal, activity tracking of stocking, and data indicating the movement of stocks to aisles. Correlating these multiple data sources provides a clean reference state vector.

Multiple data sources provide for path prediction. The path prediction is based on the statistical analysis of shopper paths taken based on dwell time in certain departments. Dwell time is generated from video data and is correlated with location data obtained from Wi-Fi data in order to predict paths for shoppers.

Illustrated in FIG. 11 is a misplaced product 1105 on shelf 1110. Video sensor 1115 and/or pressure sensor 1120 may be used to determine that product 1105 is misplaced. A risk level of nearby activity is identified. For example, it may be determined whether or not the movement of another product likely caused product 1105 to fall. Risk to customer traffic is also analyzed on a real time basis. The traffic may be identified using data from video camera 1115 to identify the location and movement of shoppers 1125a-f, or through other sources of data, such as Wi-Fi data from the mobile devices used by the shoppers 1125a-f. Furthermore, the shopper activity will be combined with what is known about the location of misplaced product 1105. A fall profile and safety risk index is created, and based on these indices, staff associates may be proactively activated, or an aisle may be closed until the risk can be lowered. The safety risk index is a derived insight based on the following:

The position of the product on the shelf.
The location of the product on the shelf.
The location of other products in the aisle.
The type of products and product removal impact in neighboring aisles.

Figure 12:
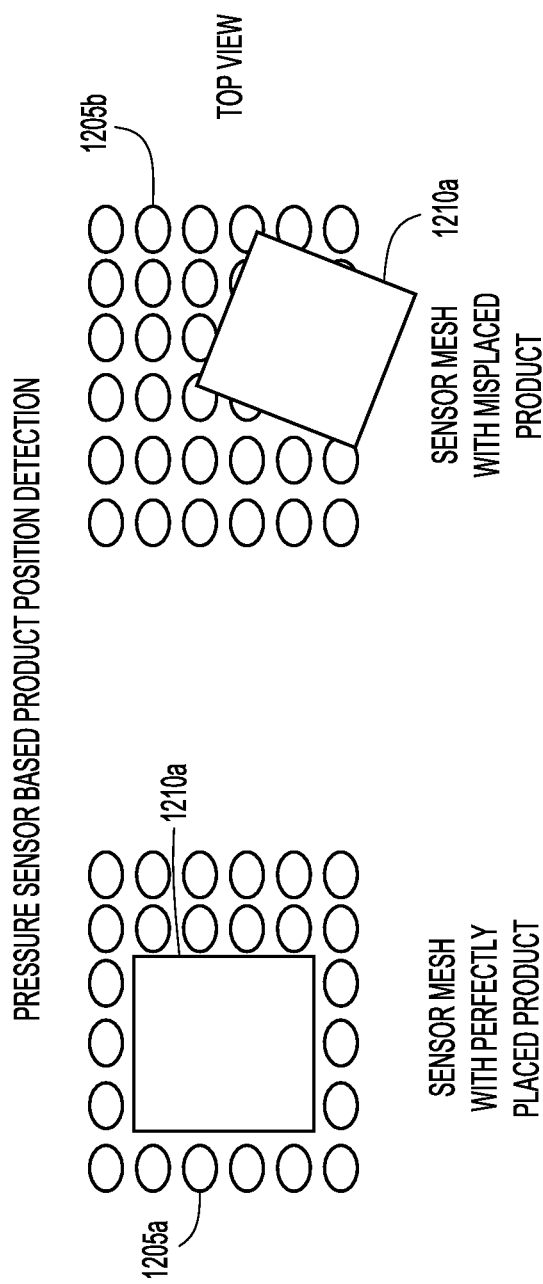
FIG. 12 is an illustration of using pressure sensors to track the physical presence of products, according to an example embodiment.

With reference now made to FIG. 12, depicted therein is an illustration of how pressure sensors may be used to determine that a product is misplaced. Illustrated are two separate pressure sensor meshes 1205a and 1205b, upon which two products 1210a and 1210b are arranged, respectively. The outputs of sensor meshes 1205a and 1205b are used to generate sensor pressure maps 1215a and 1215b, respectively. Based on the pressure sensor maps 1215a and 1215b it may be determined where the products 1210a and 1210b are located. As illustrated, product 1210b is misplaced relative to sensor mesh 1205b, and its position corresponds to the portions of pressure map 1215b that register high numeric pressure values. Furthermore, the pressure map 1215a can be compare with pressure map 1215b to determine that product 1205b is misplaced as its pressure map, pressure map 1215b, differs from pressure map 1215a for product 1205a. Furthermore, pressure maps 1215a and 1215b also provide data about the weight of products 1205a and 1205b, which will allow for risk level determinations. For example, heavy products may be determined to pose a greater risk than light weight products. Finally, the position of the product is analyzed based on the center of gravity alignment. The center of gravity alignment may be determined based on were the center of gravity, calculated from the pressure maps 1215a and 1215b, falls within pressure sensor meshes 1205a and 1205b.

Figure 13:
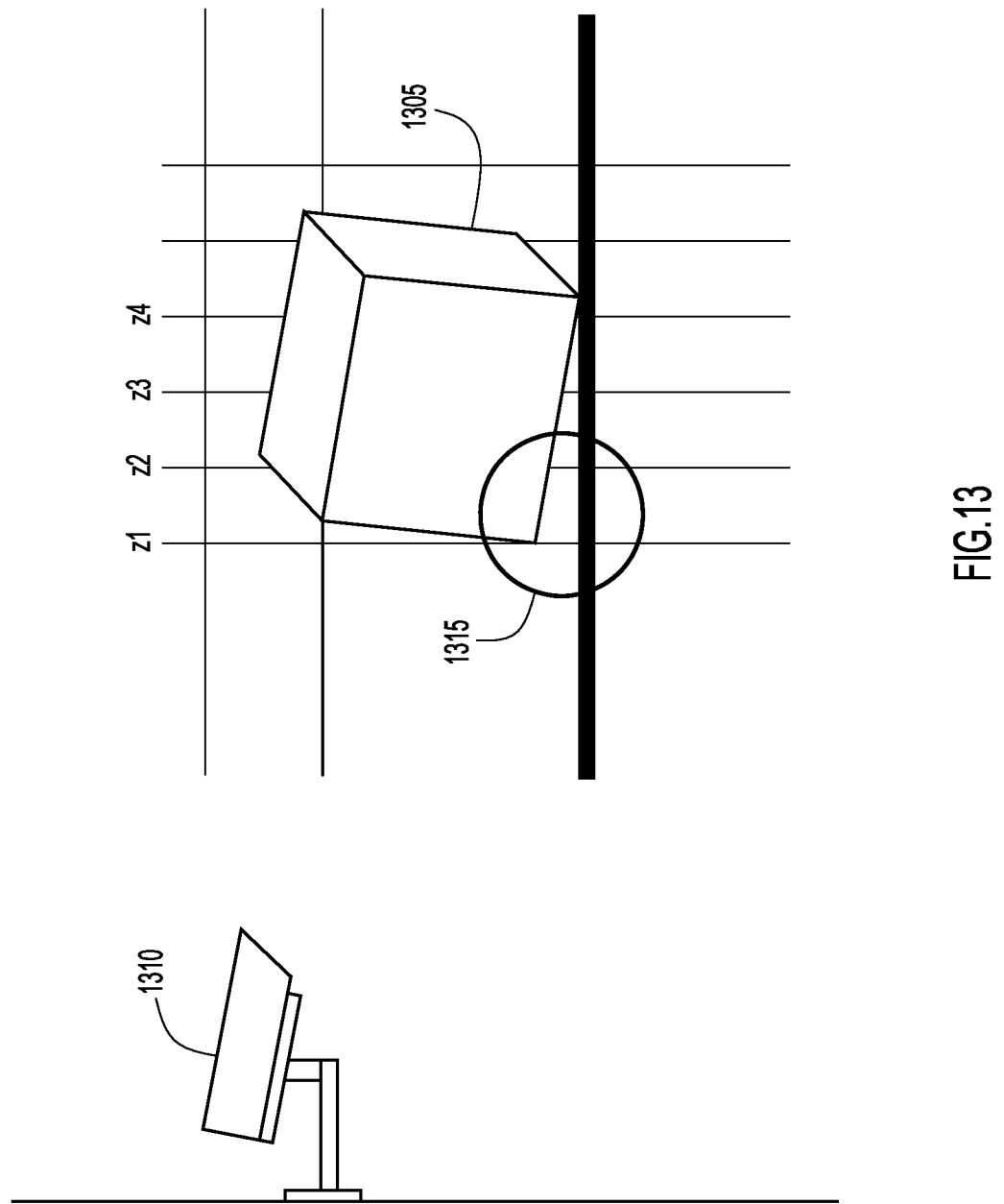
FIG. 13 is an illustration of using video data to track the physical presence of products, according to an example embodiment.

With reference now made to FIG. 13, depicted therein is an illustration of how video data from video camera 1310 may be used as a second sensor source (i.e., second to pressure sensor data as illustrated in FIG. 12). The video data may be correlated with other data (e.g., the pressure sensor data) to verify the position of the product 1305. As illustrated, camera 1310 implements step based pan/tilt modeling to determine an alignment gap. The ramp distribution of gap 1315 indicates a higher risk of fall. A ramp distribution is an indication that a product is currently in a slanting position, and therefore, has a higher probability of sliding, falling or otherwise moving. If the product is not uniformly set, the product has a greater chance of falling. For example, a product that is protruding from the shelf will have a very short shelf base product overlap, and therefore, may be likely to fall. The shelf base overlap indicates the amount of overlap between the footprint of a product and the shelf on which the product is placed. For example, if a product is laid flat on a shelf, the overlap will be at or close to 100%. However, if the product is protruding over the edge of the shelf, the shelf based overlap will be less than 100%, and related to the percentage of the product's footprint that is not on (i.e., overlapping with) the shelf. Generally, the higher the shelf base overlap, the more stable the product is. The video data may also be used to identify the product 1305 via its labeling and packaging, which may be used to determined the relative weight of product 1305, as well as the probable impact if product 1305 were to fall.

Figure 14:
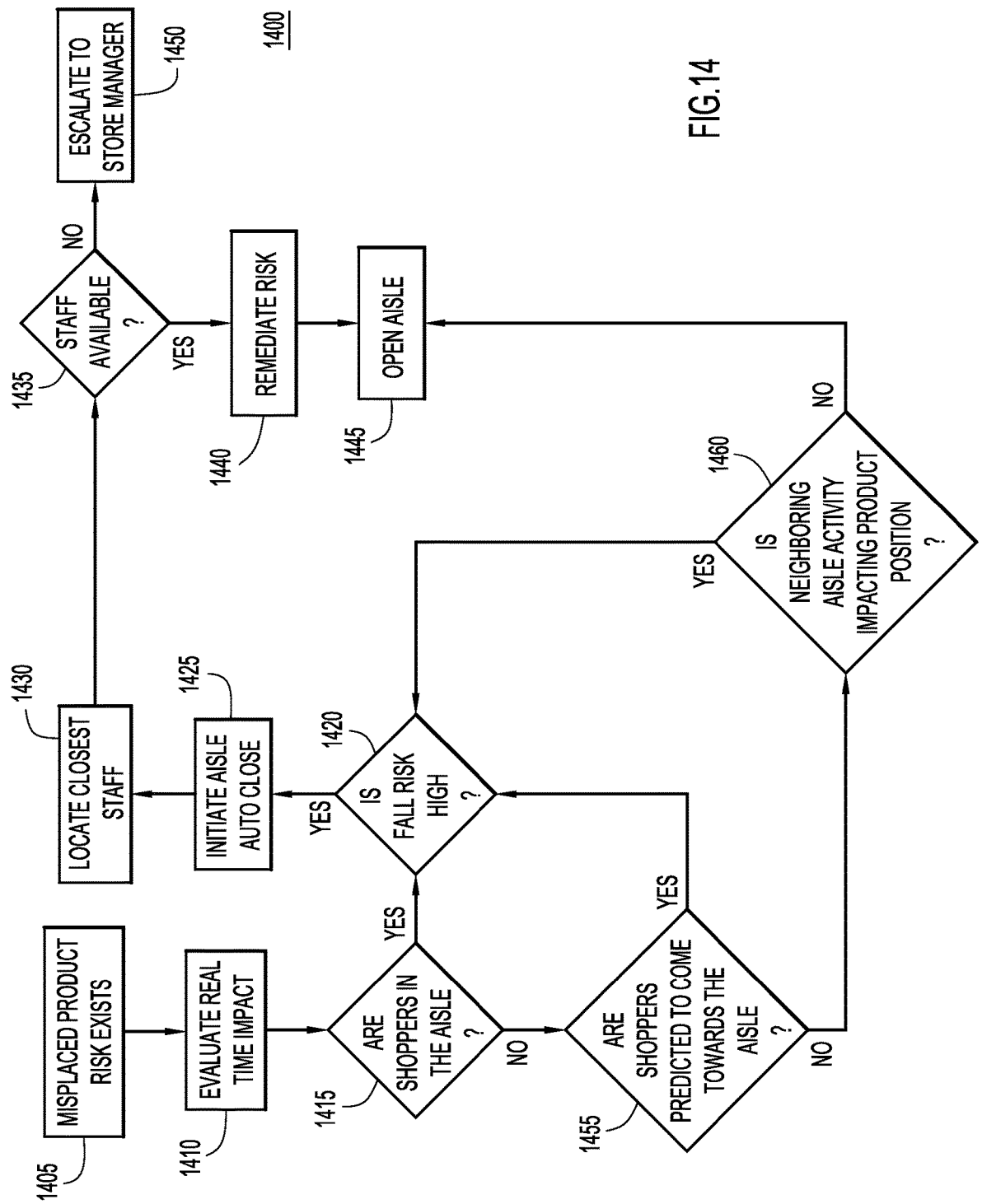
FIG. 14 is a flowchart illustrating a process for tracking the physical presence of products, assessing risk based on the physical presence, and remedying the risk, according to an example embodiment.

Accordingly, the position of the product is analyzed based on the center of gravity alignment as determined by the pressure sensors of FIG. 12, and the relative shelf base support, as determined by the video data of FIG. 13, in order to determine a risk profile for the product. Once a risk profile is identified, the time to remediate is identified using an algorithm that balances risk and efficient use of labor hours. The process for remediating the misplaced product is illustrated by flowchart 1400 of FIG. 14.

The processing of flowchart 1400 begins in operation 1405 where it is determined that there is risk from a misplaced product. This risk may be identified through data provided as illustrated in FIGS. 12 and 13. In operation 1410 the real time impact of the risk is evaluated. In operation 1415, it is determined whether or not there are shoppers in the aisle. If shoppers are present in the aisle, the process moves to operation 1420, where it is determined whether or not the risk that a product will fall is high. If the fall risk is not high, the processing stops. If it is high, the aisle is closed in operation 1425, and the nearest staff is located in 1430. If staff is determined to be available in operation 1435, the available staff remediates the risk in operation 1440 and the aisle is reopened in operation 1445. On the other hand, if it is determined in 1435 that no staff is available, the issue is escalated to a manager in operation 1450.

The determination made in 1420 regarding how high the risk of fall is may be determined according to the following formula:

Magnitude of Risk of Fall=Function (Safety risk index, the real time traffic coming into the aisle, traffic coming into the adjacent aisle, probable action in the adjacent aisle).

When the magnitude of the risk that a fall will occur exceeds a predetermined value, operation 1420 will determined that the aisle should be closed.

The determination made in 1435 regarding whether or not staff is available for remediation may be based on the following formula:

Store associate activation for remediation of situation=Function (safety risk index and severity, store associate usage levels, location of associates).

Returning to operation 1415, if it is instead determined that there are no shoppers in the aisle, the processing moves to operation 1455 where it is determined whether or not shoppers are predicted to enter the aisle. If it is predicted that shoppers are likely to enter the aisle, processing moves to operation 1420, and continues as described above. On the other hand, if shoppers are not predicted to be in the aisle, processing moves to operation 1460 where it is determined whether or not neighboring aisle activity is impacting product placement. If neighboring aisle activity is impacting product placement, the processing moves to operation 1420 and continues as described above. On the other hand, if it is determined that neighboring aisle activity is not impacting product placement, processing moves to operation 1445 where the aisle is reopened.

Figure 15:
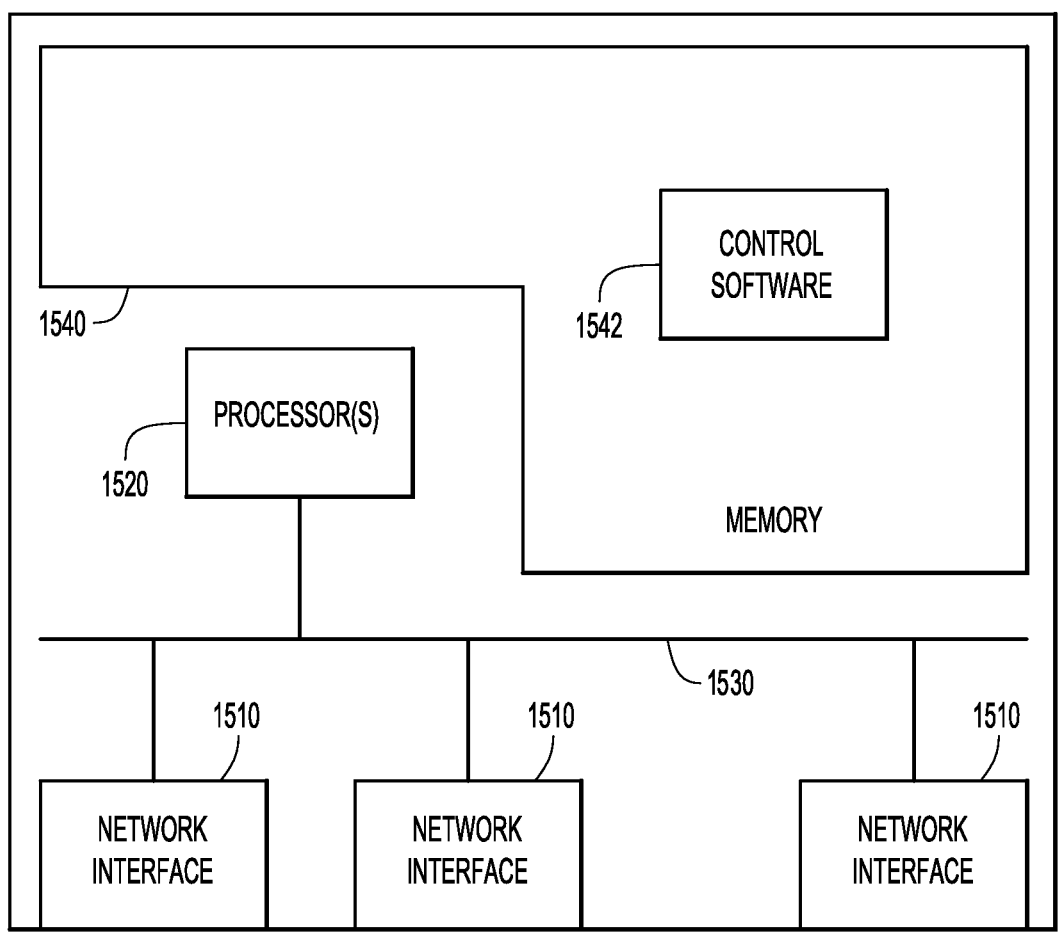
FIG. 15 is a block diagram of a device configured to combine time and motion data to generate high fidelity data sets and remedy issues, according to an example embodiment.

With reference now made to FIG. 15, an example block diagram is shown of a device 1500 that may be any one of the devices described above with reference to FIGS. 1-14. Accordingly, device 1500 is configured to perform the techniques described herein. Device 1500 includes network interfaces (e.g., network ports) 1510 which may be used to receive and send packets over a network. The network interfaces 1510 may be included as part of a network interface unit (e.g., a network interface card). Accordingly, network interfaces 1510 may be embodied as wired interfaces, wireless interfaces, optical interfaces, electrical interfaces, or a combination thereof. One or more processors 1520 are provided to coordinate and control device 1500. The processor 1520 is, for example, one or more microprocessors or microcontrollers, and it communicates with the network interfaces 1510 via bus 1530. Memory 1540 stores software instructions 1542 which may be executed by the processor 1520. For example, control software 1542 for device 1500 includes instructions for performing time and motion data sets analysis to remediate issues, as described above with reference to FIGS. 1-14. In other words, memory 1540 includes instructions for device 1500 to carry out the operations described above in connection with FIGS. 1-14. Memory 1540 may also store the data sent from data sources described above with reference to FIGS. 1-14. This data may be stored in a database in memory 1540, and control software 1542 may allow the processor 1520 to access the data.

Memory 1540 may include read only memory (ROM), random access memory (RAM), magnetic disk storage media devices, optical storage media devices, flash memory devices, electrical, optical or other physical/tangible (e.g. non-transitory) memory storage devices. Thus, in general, the memory 1540 may be or include one or more tangible (non-transitory) computer readable storage media (e.g., a memory device) encoded with software comprising computer executable instructions. When the instructions of the control software 1542 are executed (by the processor 1520), the processor is operable to perform the operations described herein in connection with FIGS. 1-14.

In summary, provided herein are methods in which a plurality of time and motion data sets are correlated at a network connected device. The time and motion data sets track an item of interest, and at least one of the time and motion data sets comprises energy consumption data or wireless local area network location data. Physical presence for the item of interest is determined based upon the correlating of the multiple time and motion data sets. Based upon the physical presence of the item of interest, an unacceptable condition for the item of interest may be determined. The unacceptable condition for the item of interest is remedied.

Also provided herein are apparatuses comprising a processor that is configured to correlate a plurality of time and motion data sets. The time and motion data sets track an item of interest, and at least one of the time and motion data sets comprises energy consumption data or wireless local area network location data. Physical presence for the item of interest is determined by the processor based upon the correlating of the multiple time and motion data sets. Based upon the physical presence of the item of interest, the processor determines that an unacceptable condition exists for the item of interest. The unacceptable condition for the item of interest is remedied through steps implemented by the processor.

Finally, provided herein are tangible, non-transitory computer readable media encoded with instructions such that when a processor executes the instructions, the processor correlates a plurality of time and motion data sets. The time and motion data sets track an item of interest, and at least one of the time and motion data sets comprises energy consumption data or wireless local area network location data. The instructions further cause the processor to determine a physical presence for the item of interest based upon the correlating of the multiple time and motion data sets. The instructions further cause the processor to determine that an unacceptable condition exists for the item of interest based upon the physical presence of the item of interest. The instructions cause the processor to take steps to remedy the unacceptable condition for the item of interest.

The above description is intended by way of example only. Although the techniques are illustrated and described herein as embodied in one or more specific examples, it is nevertheless not intended to be limited to the details shown, since various modifications and structural changes may be made within the scope and range of equivalents of the claims.

What is claimed is:

1. A method comprising:
receiving a plurality of time and motion data sets tracking a participant in an online collaborative session, wherein a first of the time and motion data sets comprises energy consumption data and/or wireless local area network location data and a second of the time and motion data sets comprises data indicative of an Area of Expected Presence of the participant in the online collaborative session;
determining an Area of Probable Presence of the participant based upon the first of the time and motion data sets;
determining that an overlap between the Area of Expected Presence and the Area of Probable Presence deviates from a threshold value;
determining, from the deviation from the threshold value, that security of the online collaborative session may be breached by the participant;
executing, in response to determining that the security of the online collaborative session may be breached by the participant, an analysis to determine an Area of Actual Presence of the participant;
determining that the Area of Expected Presence and the Area of Actual Presence do not overlap; and
applying access policies to the online collaborative session, in response to determining that the Area of Expected Presence and the Area of Actual Presence do not overlap, by requiring the participant to provide enhanced authentication to the online collaborative session.

2. The method of claim 1, wherein the online collaborative session comprises a telehealth collaborative session.

3. The method of claim 2, wherein applying access policies to the online collaborative session comprises denying the participant in the telehealth collaborative session access to the telehealth collaborative session until the participant provides the enhanced authentication.

4. The method of claim 2, wherein applying the access policies to the online collaborative session comprises requiring the participant to actively authenticate to the telehealth collaborative session.

5. An apparatus comprising:
a network interface; and
a processor, wherein the processor if configured to:
receive a plurality of time and motion data sets tracking a participant in an online collaborative session, wherein a first of the time and motion data sets comprises energy consumption data and/or wireless local area network location data and a second of the time and motion data sets comprises an Area of Expected Presence of the participant in the online collaborative session, and wherein the dime and motion data sets are received at the processor via a network connected to the network interface;

determine an Area of Probable Presence of the participant based upon the first of the time and motion data sets;

determine that an overlap between the Area of Expected Presence and the Area of Probable Presence deviates from a threshold value;

determine, from the deviation from the threshold value, that security of the online collaborative session may be breached by the participant; execute, in response to determining that the security of the online collaborative session may be breached by the participant, an analysis to determine an Area of Actual Presence of the participant; determine that the Area of Expected Presence and the Area of Actual Presence do not overlap; and apply access policies to the online collaborative session, in response to determining that the Area of Expected Presence and the Area of Actual Presence do not overlap, by requiring the participant to provide enhanced authentication to the online collaborative session.

6. The apparatus of claim 5, wherein the online collaborative session comprises a telehealth collaborative session.

7. The apparatus of claim 6, wherein the processor is configured to apply the access policies by denying the participant access to the telehealth collaborative session until the participant provides the enhanced authentication.

8. A tangible non-transitory computer readable medium encoded with instructions, wherein the instructions, when executed by a processor, cause the processor to:

receive a plurality of time and motion data sets tracking a participant in an online collaborative session, wherein a first of the time and motion data sets comprises energy consumption data and/or wireless local area network location data and a second of the time and motion data sets comprises data indicative of an Area of Expected Presence of the participant in the online collaborative session, and wherein the time and motion data sets are received at the processor via a network connected to a network interface;

determine an Area of Probable Presence of the participant based upon the first of the time and motion data sets;

determine that an overlap between the Area of Expected Presence and the Area of Probable Presence deviates from a threshold value;

determine, from the deviation from the threshold value, that security of the online collaborative session may be breached by the participant;

execute, in response to determining that the security of the online collaborative session may be breached by the participant, an analysis to determine an Area of Actual Presence of the participant;

determine that the Area of Expected Presence and the Area of Actual Presence do not overlap; and apply access policies to the online collaborative session, in response to determining that the Area of Expected Presence and the Area of Actual Presence do not overlap, by requiring the participant to provide enhanced authentication to the online collaborative session.

9. The computer readable medium of claim 8, wherein the online collaborative session comprises a telehealth collaborative session.

10. The computer readable medium of claim 9, wherein the instructions cause the processor to apply the access policies by denying the participant access to the telehealth collaborative session until the participant provides enhanced authentication.

11. The method of claim 1, wherein applying the access policies to the online collaborative session comprises applying facial recognition to the participant.

12. The method of claim 1, wherein applying the access policies to the online collaborative session comprises notifying an authorized participant or a control center of the determination that the security of the online collaborative session may be breached by the participant.

13. The method of claim 1, wherein applying the access policies to the online collaborative session comprises requiring the participant to submit to a fingerprint scan.

14. The method of claim 1, wherein applying the access policies to the online collaborative session comprises requiring the participant to submit to a retinal scan.

15. The apparatus of claim 5, wherein the processor is configured to apply the access policies by applying facial recognition to the participant.

16. The apparatus of claim 5, wherein the processor is configured to apply the access policies by notifying an authorized participant or a control center of the determination that the security of the online collaborative session may be breached by the participant.

17. The apparatus of claim 5, wherein the processor is configured to apply the access policies by requiring the participant to submit to a fingerprint scan or a retinal scan.

18. The computer readable medium of claim 8, wherein the instructions cause the processor to apply the access policies to the online collaborative session by applying facial recognition to the participant.

19. The computer readable medium of claim 8, wherein the instructions cause the processor to apply the access policies to the online collaborative session by notifying an authorized participant or a control center of the determination that the security of the online collaborative session may be breached by the participant.

20. The computer readable medium of claim 8, wherein the instructions cause the processor to apply the access policies to the online collaborative session by requiring the participant to submit to a fingerprint scan or a retinal scan.

\* \* \* \* \*

UNITED STATES PATENT AND TRADEMARK OFFICE
CERTIFICATE OF CORRECTION

PATENT NO. : 10,558,784 B2  
APPLICATION NO. : 14/845771  
DATED : February 11, 2020  
INVENTOR(S) : Rajesh Vargheese et al.

Page 1 of 1

It is certified that error appears in the above-identified patent and that said Letters Patent is hereby corrected as shown below:

In the Claims

Claim 5, Column 18, Line 64, please replace "if configured to:" with --is configured to:--  
Claim 5, Column 19, Line 5, please replace "the dime and" with --the time and--

Signed and Sealed this  
Seventeenth Day of March, 2020

Andrei Iancu  
*Director of the United States Patent and Trademark Office*